United States Patent
Chassaing et al.

(10) Patent No.: US 10,010,538 B2
(45) Date of Patent: Jul. 3, 2018

(54) **USE OF ANTHELMINTIC AGENTS AGAINST *DIROFILARIA IMMITIS***

(71) Applicant: Intervet Inc., Madison, NJ (US)

(72) Inventors: Christophe Pierre Alain Chassaing, Ingelheim am Rhein (DE); Jurgen Lutz, Wiesbaden (DE); Anja Regina Heckeroth, Stadecken-Elsheim (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/324,875

(22) PCT Filed: Jul. 10, 2015

(86) PCT No.: PCT/EP2015/065868
§ 371 (c)(1),
(2) Date: Jan. 9, 2017

(87) PCT Pub. No.: WO2016/005576
PCT Pub. Date: Jan. 14, 2016

(65) Prior Publication Data
US 2017/0202816 A1    Jul. 20, 2017

(30) Foreign Application Priority Data

Jul. 11, 2014  (EP) ..................................... 14176733

(51) Int. Cl.
*A61K 31/445* (2006.01)
(52) U.S. Cl.
CPC .................................. *A61K 31/445* (2013.01)
(58) Field of Classification Search
CPC .................................................... A61K 31/445
USPC ........................................................ 514/327
See application file for complete search history.

(56) References Cited

U.S. PATENT DOCUMENTS

| 5,994,395 A | 11/1999 | Lowndes et al. |
| 2014/0142114 A1 | 5/2014 | Meng et al. |

FOREIGN PATENT DOCUMENTS

| EP | 2468096 A1 | 6/2012 |
| WO | 2009077527 A1 | 6/2009 |
| WO | 2010115688 A1 | 10/2010 |
| WO | 2010146083 A1 | 12/2010 |
| WO | 2014081697 A2 | 5/2014 |

OTHER PUBLICATIONS

Dirofilariasis Frequently Asked Questions (FAQs), Center for Disease Control and Prevention (CDC), Atlanta, USA.*
Extended EP search report for 14175733.5 dated Feb. 27, 2015.
International Search Report for PCTEP2015065868 dated Sep. 17, 2015. 4 Pages.
American Heartworm Society, Heartworm Life Cycle Illustration, For Pet Owners; Dog & Cat Heartworm Combined Life Cycle Posters; https://www.heartwormsociety.org/images/pdf/AHS2014HWLifeCycleCLIENTCLR.pdf; Oct. 17, 2017; p. 1.
Atkins, Clarke et al., Overview of Heartworm Disease, (Dirofilarosis, Dirofilariasis); Circulatory System, Heartworm Disease; http://www.merckvetmanual.com/circulatory-system/heartworm-disease/overview-of-heartworm-disease; Oct. 17, 2017, pp. 1-17.
Vercruysse, Jozef et al., Benzimidazoles, Pharamacology; http://www.merckvetmanual.com/pharmacology/anthelmintics/benzimidazoles; Oct. 17, 2017, pp. 1-3.
Office Action dated Apr. 20, 2018 for U.S. Appl. No. 15/324,806, 12 pages.

* cited by examiner

*Primary Examiner* — Taofiq A Solola

(57) ABSTRACT

This invention is directed to compounds and salts that are generally useful as agents to treat an infection with *Dirofilaria immitis*. This invention also is directed to treatments comprising the administration of the compounds and salts to animals in need of the treatments.

1 Claim, No Drawings

USE OF ANTHELMINTIC AGENTS AGAINST *DIROFILARIA IMMITIS*

CROSS-REFERENCE TO RELATED APPLICATIONS

This application is a national stage entry under 35 U.S.C. § 371 of PCT/EP2015/065868, filed on Jul. 10, 2015, which claims priority to EP Application No. EP14176733.5, filed on Jul. 11, 2014, the content of PCT/EP2015/065868 is hereby incorporated by reference in its entirety.

FIELD OF THE INVENTION

This invention relates to compounds and salts thereof that are generally useful as agents against *Dirofilaria immitis*. This invention also relates to treatments comprising the administration of the compounds and salts thereof to animals in need of the treatments.

BACKGROUND OF THE INVENTION

Heartworm infection is caused by a filarial organism, *Dirofilaria immitis*. At least 70 species of mosquitoes can serve as intermediate hosts; *Aedes, Anopheles* and *Culex* are the most common genera acting as vectors. Patent infections are possible in numerous wild and companion animal species. Wild animal reservoirs include wolves, coyotes, foxes, California gray seals, sea lions, and raccoons. In companion animals, heartworm infection is diagnosed primarily in dogs and less commonly in cats and ferrets. Heartworm disease has been reported in most countries with temperate, semi-tropical, or tropical climates, including the USA, Canada, Australia, Latin America, and southern Europe. In companion animals, infection risk is greatest in dogs and cats housed outdoors, but any dog or cat, indoor or outdoor, is capable of being infected.

Mosquito vector species acquire microfilaria (a neonatal larval stage) while feeding on an infected host. Once ingested by the mosquito, development of microfilariae into the first larval stage (L1) occurs. They then actively molt into the second larval stage (L2) and again to the infective third stage (L3) within the mosquito in 1 to 4 weeks, depending on environmental temperatures. When mature, the infective larvae migrate to the labium of the mosquito. As the mosquito feeds, the infective larvae erupt through the tip of the labium with a small amount of hemolymph onto the host's skin. The larvae migrate into the bite wound, beginning the mammalian portion of their life cycle. In canids and other susceptible hosts, infective larvae (L3) molt into a fourth stage (L4) in 3 to 12 days. After remaining in the subcutaneous tissue, abdomen, and thorax for about 2 months, the L4 larvae undergo their final molt at day 50 to 70 into young adults, arriving in the heart and pulmonary arteries about 70 to 120 days following initial infection.

The only available heartworm adulticide is melarsomine dihydrochloride, which is effective against mature (adult) and immature heartworms of both genders. Heartworm infection is preventable with macrolide prophylaxis. Year-round prevention is advised because of the potential for severe consequences, regardless of the housing status of the animals. Formulations of the macrolide preventives ivermectin, milbemycin oxime, moxidectin, and selamectin are safe and effective as prescribed for all breeds of dogs. Ivermectin/pyrantel pamoate (hookworms and roundworms) and milbemycin (hookworms, roundworms, and whipworms) also provide control of intestinal nematodes. At the approved dose, milbemycin kills microfilariae quickly, and in the face of high microfilarial concentrations a shock reaction may occur. Thus, milbemycin should not be administered without close monitoring as a preventive in dogs with high numbers of microfilariae. Ivermectin for cats is safe and effective at 24 µg/kg, PO, once monthly. Formulations of selamectin and a combination of imidacloprid/moxidectin are labeled for both dogs and cats.

Inter alia due to the possibility of resistance against existing drugs, there is a continuous need for finding new drugs that are active against *Dirofilaria immitis* (which includes any of the non-adult animal stages of the organism), which drugs can be used to treat an infection therewith (which treatment may by to prevent the infection or to therapeutically reduce the infection).

SUMMARY OF THE INVENTION

Briefly, this invention is related to compounds and salts thereof that can generally be used to treat an infection with *Dirofilaria immitis*. The compounds correspond in structure to Formula I:

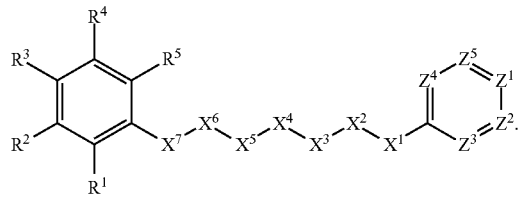

In Formula (I), each of $R^1$, $R^2$, $R^3$, $R^4$, and $R^5$ is independently selected from the group consisting of hydrogen, halogen, cyano, alkyl, alkoxy, nitro, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

$X^1$ is selected from the group consisting of —O—, —C(O)—, —S—, —S(O)—, —S(O)$_2$—, and —NH—. The —NH— is optionally substituted with a substituent selected from the group consisting of alkyl, alkenyl, alkynyl, alkoxyalkyl, carbocyclyl, and carbocyclylalkyl. Any such substituent is optionally substituted with one or more independently selected halogen.

$X^2$ is selected from the group consisting of straight-chain $C_3$-$C_5$-alkyl, straight-chain $C_3$-$C_5$-alkenyl, straight-chain $C_3$-$C_5$-alkynyl, and $C_4$-$C_6$-carbocyclyl. The straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected alkyl.

$X^3$ is selected from the group consisting of —CH$_2$—, —O—, —C(O)—, —S—, —S(O)—, —S(O)$_2$—, and —NH—. The —CH$_2$— is optionally substituted with up to two substituents independently selected from the group consisting of alkyl and carbocyclyl. The —NH— is optionally substituted with a substituent selected from the group consisting of alkyl, alkenyl, alkynyl, alkoxyalkyl, carbocyclyl, and carbocyclylalkyl. Any such substituent of —NH— is optionally substituted with one or more independently selected halogen.

$X^4$ is selected from the group consisting of —CH$_2$— and —NH—. The —CH$_2$— is optionally substituted with up to two substituents independently selected from the group consisting of alkyl, haloalkyl, and alkenyl. The —NH— is optionally substituted with a substituent selected from the group consisting of alkyl, alkenyl, alkynyl, alkoxy alkyl, carbocyclyl, and carbocyclylalkyl. Any such substituent of —NH— is optionally substituted with one or more independently selected halogen.

$X^5$ is selected from the group consisting of —CH$_2$—, —O—, —C(S)—, —C(O)—, —S(O)—, and —S(O)$_2$—. The —CH$_2$— is optionally substituted with up to two substituents independently selected from the group consisting of alkyl and carbocyclyl.

$X^6$ is a linker. The linker is a hydrocarbon group, wherein: (a) the linker comprises one or more nitrogen atoms, and (b) one or more of the carbons in the hydrocarbon optionally are substituted with one or more substituents independently selected from the group consisting of oxo, thiocarbonyl, halogen, hydroxy, and alkoxy. The linker comprises at least one chain of from 3 to 6 atoms that bridges $X^5$ to $X^7$. From 1 to 2 of the chain atoms are nitrogen. The linker has no chain of less than 3 atoms that bridges $X^5$ and $X^7$.

$X^7$ is selected from the group consisting of a bond, —O—, —C(O)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$—. The —NH— is optionally substituted with alkyl. The —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$— are optionally substituted with one or more independently selected alkyl.

$Z^1$ is selected from the group consisting of N and CH. The CH is substituted with a substituent selected from the group consisting of halogen, nitro, cyano, aminosulfonyl, alkyl, alkoxy, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl. The alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl; and the aminosulfonyl is optionally substituted with up to two independently selected alkyl.

$Z^2$ is selected from the group consisting of N and CH. The CH is optionally substituted with a substituent selected from the group consisting of cyano, halogen, nitro, alkyl, alkoxy, haloalkyl, and haloalkylsulfanyl.

Each of $Z^3$, $Z^4$, and $Z^5$ is independently selected from the group consisting of N and CH. The CH is optionally substituted with a substituent selected from the group consisting of halogen, cyano, nitro, alkyl, alkoxy, alkylsulfanyl, haloalkyl, haloalkoxy, and haloalkylsulfanyl.

This invention also is directed, in part, to methods for treating an infection with *Dirofilaria immitis* in an animal, in particular a dog. The methods comprise administering at least one compound or salt of this invention to the animal.

This invention also is directed, in part, to a kit. The kit comprises at least one compound or salt of this invention packed in a container (vial, bag, box, sachet, syringe, blister etc.). In addition, the kit comprises at least one other component, such as another ingredient (e.g., an excipient or active ingredient, i.e. an ingredient being suitable for any medical use, preferably an anthelminthic ingredient), instructions and/or an apparatus for combining the compound or salt with another ingredient, instructions and/or an apparatus for administering the compound or salt, and/or a diagnostic tool.

It is noted that the compounds for use in the present invention may also be used to treat a helminth infection caused by one or more helminths selected from the group consisting of *Anaplocephala* spp.; *Dipylidium* spp; *Diphyllobothrium* spp.; *Echinococcus* spp.; *Moniezia* spp.; *Taenia* spp.; *Dicrocoelium* spp.; *Fasciola* spp.; *Paramphistomum* spp.; *Schistosoma* spp.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp.; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp.; *Necator* spp.; *Nematodirus* spp.; *Nippostrongylus* spp.; *Oesophagostomum* spp.; *Onchocerca* spp.; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp. and *Wuchereria* spp.

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

I. Compounds for Use According to the Invention

The compounds for use according to the invention generally correspond in structure to Formula (I):

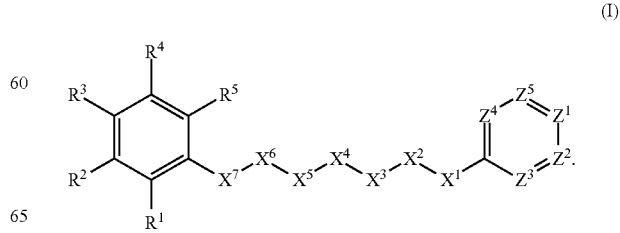

(I)

The substituents in Formula (I) are defined as follows:

A. Preferred Embodiments of $R^1$, $R^2$, $R^3$, $R^4$, and $R^5$

Each of $R^1$, $R^2$, $R^3$, $R^4$, and $R^5$ is independently selected from the group consisting of hydrogen, halogen, cyano, alkyl, alkoxy, nitro, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

In some embodiments, each of $R^1$, $R^2$, $R^3$, $R^4$, and $R^5$ is independently selected from the group consisting of hydrogen, halogen, cyano, alkyl, alkoxy, nitro, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

In some embodiments, $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, nitro, $C_1$-$C_6$-alkoxycarbonyl, $C_1$-$C_6$-alkylsulfanyl, aryl, aryloxy, aryl-$C_1$-$C_6$-alkoxy, arylsulfanyl, aryl-$C_1$-$C_6$-alkylsulfanyl, heteroaryl, heteroaryloxy, heteroaryl-$C_1$-$C_6$-alkoxy, heteroarylsulfanyl, and heteroaryl-$C_1$-$C_6$-alkylsulfanyl. The $C_1$-$C_6$-alkyl, $C_1$-$C_6$-alkoxy, $C_1$-$C_6$-alkoxycarbonyl, $C_1$-$C_6$-alkylsulfanyl, aryl, aryloxy, aryl-$C_1$-$C_6$-alkoxy, arylsulfanyl, aryl-$C_1$-$C_6$-alkylsulfanyl, heteroaryl, heteroaryloxy, heteroaryl-$C_1$-$C_6$-alkoxy, heteroarylsulfanyl, and heteroaryl-$C_1$-$C_6$-alkylsulfanyl are optionally substituted with one or more substituents independently selected from the group consisting of halogen, cyano, $C_1$-$C_6$-alkyl, $C_1$-$C_6$-alkoxy, halo-$C_1$-$C_6$-alkyl, halo-$C_1$-$C_6$-alkoxy, $C_1$-$C_6$-alkylsulfanyl, and halo-$C_1$-$C_6$-alksulfanyl. In some such embodiments, each aryl is phenyl, and each heteroaryl is a 5- to 6-member heteroaryl.

In some embodiments, $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy.

In some embodiments, $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen and halo-$C_1$-$C_6$-alkyl.

In some embodiments, $R^1$, $R^2$, $R^3$, $R^4$, and $R^5$ are each independently selected from the group consisting of hydrogen, chloro, fluoro, cyano, nitro, methyl, tert-butyl, n-propyl, trifluoromethyl, ethyl, methoxy, ethoxy, trifluoromethoxy, trifluoromethylsulfanyl, iso-butoxy, phenyl, phenoxy, benzyloxy, and 4-trifluoromethylbenzyloxy.

In some embodiments, $R^1$, $R^2$, $R^3$, $R^4$, and $R^5$ are each independently selected from the group consisting of hydrogen, halogen, cyano, and $C_1$-$C_6$-alkyl. In some such embodiments, $R^1$, $R^2$, $R^3$, $R^4$, and $R^5$ are each independently selected from the group consisting of hydrogen, fluoro, chloro, cyano, methyl, ethyl, n-propyl, and tert-butyl.

In some embodiments, $R^1$, $R^2$, $R^3$, $R^4$, and $R^5$ are each independently selected from the group consisting of hydrogen and halogen. In some such embodiments, $R^1$, $R^2$, $R^3$, $R^4$, and $R^5$ are each independently selected from the group consisting of hydrogen, chloro, and fluoro. In other embodiments, $R^1$, $R^2$, $R^3$, $R^4$, and $R^5$ are each independently selected from the group consisting of hydrogen and fluoro. In still other embodiments, $R^1$, $R^2$, $R^3$, $R^4$, and $R^5$ are each independently selected from the group consisting of hydrogen and chloro.

In some embodiments, $R^1$, $R^2$, $R^3$, $R^4$, and $R^5$ are each independently selected from the group consisting of hydrogen and cyano.

In some embodiments, $R^1$, $R^2$, $R^3$, $R^4$, and $R^5$ are each independently selected from the group consisting of hydrogen and trifluoromethyl.

In some embodiments, $R^1$, $R^2$, $R^3$, $R^4$, and $R^5$ are each independently selected from the group consisting of hydrogen, phenyl, and $C_1$-$C_6$-alkylphenyl.

In some embodiments, $R^1$, $R^2$, $R^3$, $R^4$, and $R^5$ are each independently selected from the group consisting of hydrogen and $C_1$-$C_6$-alkyl. In some such embodiments, $R^1$, $R^2$, $R^3$, $R^4$, and $R^5$ are each independently selected from the group consisting of hydrogen, methyl, ethyl, n-propyl, and tert-butyl. In other embodiments, $R^1$, $R^2$, $R^3$, $R^4$, and $R^5$ are each independently selected from the group consisting of hydrogen and methyl. In other embodiments, $R^1$, $R^2$, $R^3$, $R^4$, and $R^5$ are each independently selected from the group consisting of hydrogen and ethyl. In other embodiments, $R^1$, $R^2$, $R^3$, $R^4$, and $R^5$ are each independently selected from the group consisting of hydrogen and n-propyl. In still other embodiments, $R^1$, $R^2$, $R^3$, $R^4$, and $R^5$ are each independently selected from the group consisting of hydrogen and tert-butyl.

In some embodiments, one of $R^1$, $R^2$, $R^3$, $R^4$, and $R^5$ is hydrogen; and the remaining four of $R^1$, $R^2$, $R^3$, $R^4$, and $R^5$ are each other than hydrogen. In some such embodiments, $R^3$ is one of the substituents that is other than hydrogen.

In some embodiments, two of $R^1$, $R^2$, $R^3$, $R^4$, and $R^5$ are each hydrogen; and the remaining three of $R^1$, $R^2$, $R^3$, $R^4$, and $R^5$ are each other than hydrogen. In some such embodiments, $R^3$ is one of the substituents that is other than hydrogen. For example, in some such embodiments, $R^2$, $R^3$, and $R^4$ are the three substituents that are each other than hydrogen. In other embodiments, $R^1$, $R^3$, and $R^5$ are the substituents that are each other than hydrogen. In still other embodiments, $R^1$, $R^3$, and $R^4$ are the substituents that are each other than hydrogen.

In some embodiments, three of $R^1$, $R^2$, $R^3$, $R^4$, and $R^5$ are each hydrogen; and the remaining two of $R^1$, $R^2$, $R^3$, $R^4$, and $R^5$ are each other than hydrogen. In some such embodiments, $R^3$ is one of the substituents that is other than hydrogen. For example, in some such embodiments, $R^2$ and $R^3$ are the two substituents that are each other than hydrogen. In other embodiments, $R^1$ and $R^3$ are the two substituents that are each other than hydrogen. In other embodiments, $R^1$ and $R^2$ are the two substituents that are each other than hydrogen.

In some embodiments, four of $R^1$, $R^2$, $R^3$, $R^4$, and $R^5$ are each hydrogen; and the remaining one of $R^1$, $R^2$, $R^3$, $R^4$, and $R^5$ is other than hydrogen. In some embodiments, $R^3$ is the substituent that is other than hydrogen.

In some embodiments, all of $R^1$, $R^2$, $R^3$, $R^4$, and $R^5$ are each hydrogen.

In some embodiments, $R^3$ is selected from the group consisting of halogen, cyano, alkyl, alkoxy, nitro, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

In some embodiments, $R^3$ is selected from the group consisting of halogen, cyano, $C_1$-$C_6$-alkyl, $C_1$-$C_6$-alkoxy, nitro, $C_1$-$C_6$-alkoxycarbonyl, $C_1$-$C_6$-alkylsulfanyl, aryl, aryloxy, aryl-$C_1$-$C_6$-alkoxy, arylsulfanyl, aryl-$C_1$-$C_6$-alkylsulfanyl, heteroaryl, heteroaryloxy, heteroaryl-$C_1$-$C_6$-alkoxy, heteroarylsulfanyl, and heteroaryl-$C_1$-$C_6$-alkylsulfanyl. The $C_1$-$C_6$-alkyl, $C_1$-$C_6$-alkoxy, $C_1$-$C_6$-alkoxycarbonyl, $C_1$-$C_6$-alkylsulfanyl, aryl, aryloxy, aryl-$C_1$-$C_6$-alkoxy, arylsulfanyl, aryl-$C_1$-$C_6$-alkylsulfanyl, heteroaryl, heteroaryloxy, heteroaryl-$C_1$-$C_6$-alkoxy, heteroarylsulfanyl, and heteroaryl-$C_1$-$C_6$-alkylsulfanyl are optionally substituted with one or more substituents independently selected from the group consisting of halogen, cyano, $C_1$-$C_6$-alkyl, $C_1$-$C_6$-alkoxy, halo-$C_1$-$C_6$-alkyl, halo-$C_1$-$C_6$-alkoxy, $C_1$-$C_6$-alkylsulfanyl, and halo-$C_1$-$C_6$-alksulfanyl. In some such embodiments, each aryl is phenyl, and each heteroaryl is a 5- to 6-member heteroaryl.

In some embodiments, $R^3$ is selected from the group consisting of halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy.

In some embodiments, $R^3$ is selected from the group consisting of halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen and halo-$C_1$-$C_6$-alkyl.

In some embodiments, $R^3$ is selected from the group consisting of chloro, fluoro, cyano, nitro, methyl, tert-butyl, n-propyl, trifluoromethyl, ethyl, methoxy, ethoxy, trifluoromethoxy, trifluoromethylsulfanyl, iso-butoxy, phenyl, phenoxy, benzyloxy, and 4-trifluoromethylbenzyloxy.

In some embodiments, $R^3$ is chloro.
In some embodiments, $R^3$ is fluoro.
In some embodiments, $R^3$ is cyano.
In some embodiments, $R^3$ is methyl.
In some embodiments, $R^3$ is ethyl.
In some embodiments, $R^3$ is n-propyl.
In some embodiments, $R^3$ is tert-butyl.
In some embodiments, $R^3$ is trifluoromethyl.

B. Preferred Embodiments of $X^1$ $X^1$ is selected from the group consisting of —O—, —C(O)—, —S—, —S(O)—, —S(O)$_2$—, and —NH—.

Here, the —NH— is optionally substituted with a substituent selected from the group consisting of alkyl, alkenyl, alkynyl, alkoxyalkyl, carbocyclyl, and carbocyclylalkyl. Any such substituent is optionally substituted with one or more independently selected halogen.

In some embodiments, $X^1$ is selected from the group consisting of —O—, —C(O)—, —S—, —S(O)—, —S(O)$_2$—, and —NH—. Here, the —NH— is optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. Any such substituent is optionally substituted with one or more independently selected halogen.

In some embodiments, $X^1$ is —O—. In such embodiments, the compound is encompassed by the following formula:

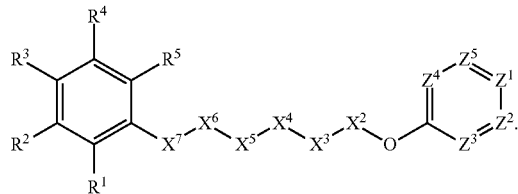

In some embodiments, $X^1$ is —NH— optionally substituted with $C_1$-$C_6$-alkyl. To illustrate, in some such embodiments, $X^1$ is —NH—. In such embodiments, the compound is encompassed by the following formula:

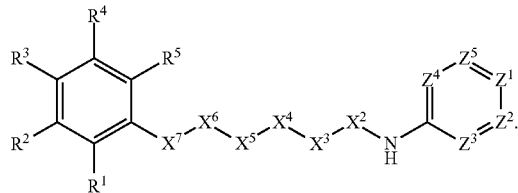

In other embodiments, for example, $X^1$ is —N(CH$_3$)—. Here, the compound is encompassed by the following formula:

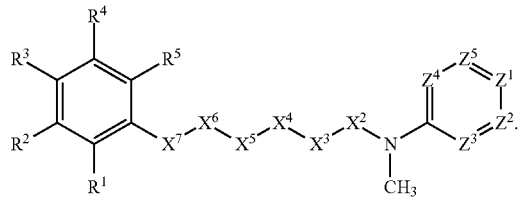

C. Preferred Embodiments of $X^2$ $X^2$ is selected from the group consisting of straight-chain $C_3$-$C_5$-alkyl, straight-chain $C_3$-$C_5$-alkenyl, straight-chain $C_3$-$C_5$-alkynyl, and $C_4$-$C_6$-carbocyclyl. The straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected alkyl. In some such embodiments, the straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected $C_1$-$C_6$-alkyl.

In some embodiments, $X^2$ is selected from the group consisting of straight-chain $C_3$-$C_5$-alkyl, straight-chain $C_3$-$C_5$-alkenyl, and straight-chain $C_3$-$C_5$-alkynyl. The straight-chain $C_3$-$C_5$-alkyl, straight-chain $C_3$-$C_5$-alkenyl, straight-chain and $C_3$-$C_5$-alkynyl are optionally substituted with one or more independently selected $C_1$-$C_6$-alkyl.

In some embodiments, $X^2$ is straight-chain $C_3$-$C_4$-alkyl optionally substituted with one or more independently selected $C_1$-$C_6$-alkyl.

In some embodiments, $X^2$ is straight-chain $C_3$-alkyl (i.e., n-propyl). In these embodiments, the compound is encompassed by the following formula:

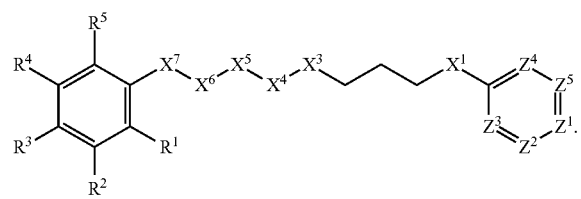

In some embodiments, $X^2$ is straight-chain $C_4$-alkyl (i.e., n-butyl). In these embodiments, the compound is encompassed by the following formula:

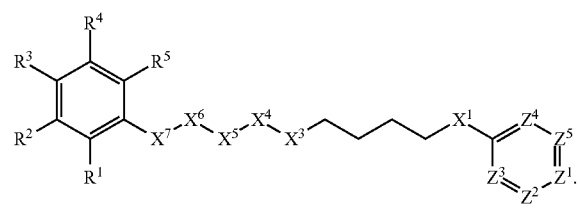

In some embodiments, $X^2$ is straight-chain $C_3$-$C_4$-alkenyl optionally substituted with one or more independently selected $C_1$-$C_6$-alkyl.

In some embodiments, $X^2$ is straight-chain $C_3$-$C_4$-alkenyl.

In some embodiments, $X^2$ is straight-chain $C_3$-$C_4$-alkynyl optionally substituted with one or more independently selected $C_1$-$C_6$-alkyl.

In some embodiments, $X^2$ is straight-chain $C_3$-$C_4$-alkynyl.

In some embodiments, $X^2$ is $C_4$-$C_6$ carbocyclyl optionally substituted with one or more independently selected $C_1$-$C_6$-alkyl.

In some embodiments, $X^2$ is a ring structure selected from the group consisting of cyclobutyl, cyclopentyl, cyclopentenyl, cyclohexyl, and phenyl. Any such group is optionally substituted with one or more independently selected $C_1$-$C_6$-alkyl.

In some embodiments, $X^2$ is cyclobutyl. In some such embodiments, the compound is encompassed by the following formula:

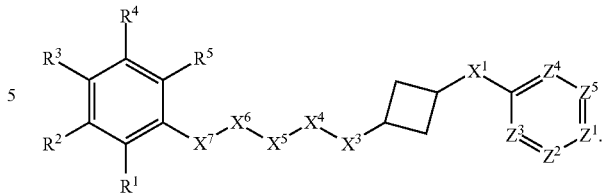

In some embodiments, $X^2$ is cyclopentyl. In some such embodiments, the compound is encompassed by the following formula:

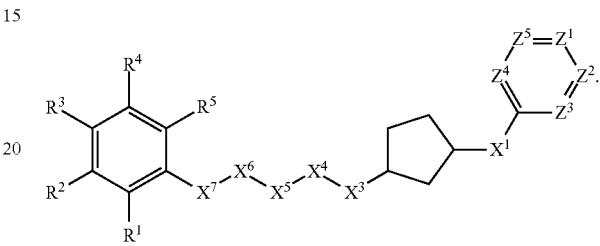

In some embodiments, $X^2$ is cyclohexyl. In some such embodiments, the compound is encompassed by the following formula:

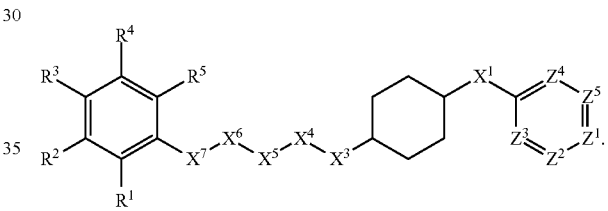

D. Preferred Embodiments of $X^3$ $X^3$ is selected from the group consisting of —O—, —C(O)—, —S—, —S(O)—, —S(O)$_2$—, —CH$_2$—, and —NH—. The —CH$_2$— is optionally substituted with up to two substituents independently selected from the group consisting of alkyl and carbocyclyl. The —NH— is optionally substituted with a substituent selected from the group consisting of alkyl, alkenyl, alkynyl, alkoxyalkyl, carbocyclyl, and carbocyclylalkyl. Any such substituent of —NH— is optionally substituted with one or more independently selected halogen.

In some embodiments, $X^3$ is selected from the group consisting of —O—, —C(O)—, —S—, —S(O)—, —S(O)$_2$—, —CH$_2$—, and —NH—. The —CH$_2$— is optionally substituted with up to two substituents independently selected from the group consisting of $C_1$-$C_6$-alkyl and cycloalkyl (e.g., $C_3$-$C_6$-cycloalkyl, such as cyclopropyl). The —NH— is optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. Any such substituent of —NH— is optionally substituted with one or more independently selected halogen.

In some embodiments, $X^3$ is —O—. In such embodiments, the compound is encompassed by the following formula:

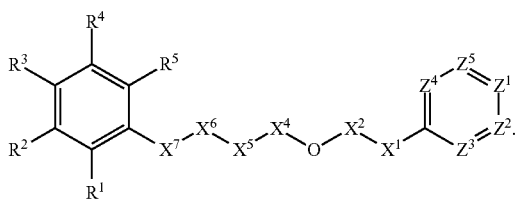

In some embodiments, $X^3$ is —$CH_2$—. In those embodiments, the compound is encompassed by the following formula:

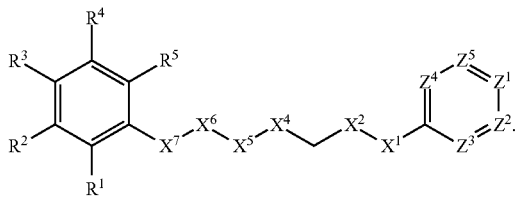

E. Preferred Embodiments of $X^4$ $X^4$ is selected from the group consisting of —$CH_2$— and —NH—. The —$CH_2$— is optionally substituted with up to two substituents independently selected from the group consisting of alkyl, haloalkyl, and alkenyl. The —NH— is optionally substituted with a substituent selected from the group consisting of alkyl, alkenyl, alkynyl, alkoxyalkyl, carbocyclyl, and carbocyclylalkyl. Any such substituent of —NH— is optionally substituted with one or more independently selected halogen.

In some embodiments, $X^4$ is selected from the group consisting of —$CH_2$— and —NH—. The —$CH_2$— is optionally substituted with up to two substituents independently selected from the group consisting of alkyl and alkenyl. The —NH— is optionally substituted with a substituent selected from the group consisting of alkyl, alkenyl, alkynyl, alkoxyalkyl, carbocyclyl, and carbocyclylalkyl. Any such substituent of —NH— is optionally substituted with one or more independently selected halogen.

In some embodiments, $X^4$ is selected from the group consisting of —$CH_2$— and —NH—. The —$CH_2$— is optionally substituted with up to two substituents independently selected from the group consisting of $C_1$-$C_6$-alkyl and $C_2$-$C_6$-alkenyl. The —NH— is optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. Any such substituent of —NH— is optionally substituted with one or more independently selected halogen.

In some embodiments, $X^4$ is —$CH_2$—. In such embodiments, the compound is encompassed by the following formula:

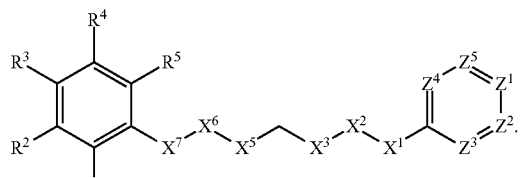

In some embodiments, $X^4$ is —$CH_2$— substituted with up to two independently selected $C_1$-$C_6$-alkyl. For example, in some embodiments, $X^4$ is —$CH_2$— substituted with methyl. In such embodiments, the compound is encompassed by the following formula:

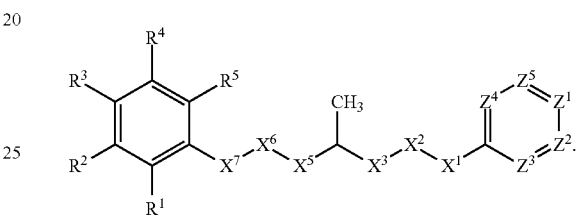

In other embodiments, $X^4$ is —$CH_2$— substituted with two methyl groups. In such embodiments, the compound is encompassed by the following formula:

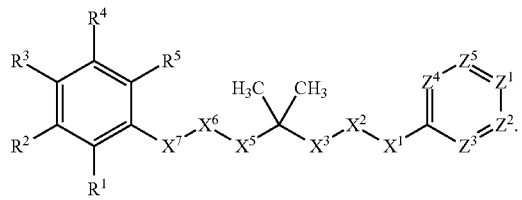

In some embodiments, $X^4$ is —$CH_2$— substituted with up to two independently selected $C_1$-$C_6$-haloalkyl. For example, in some embodiments, $X^4$ is —$CH_2$— substituted with trifluoromethyl. In such embodiments, the compound is encompassed by the following formula:

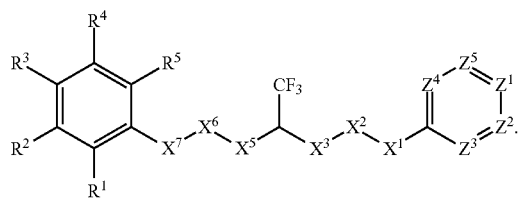

In other embodiments, $X^4$ is —$CH_2$— substituted with two trifluoromethyl groups. In such embodiments, the compound is encompassed by the following formula:

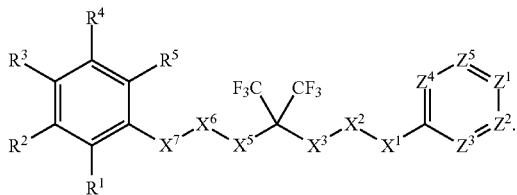

In some embodiments, $X^4$ is —NH—. In such embodiments, the compound is encompassed by the following formula:

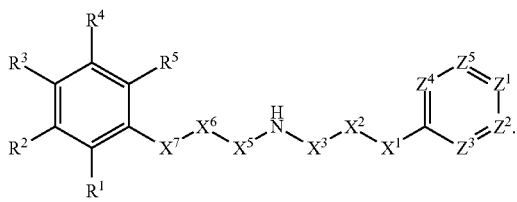

In some embodiments, $X^4$ is —NH— substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. In some such embodiments, $X^4$ is —NH— substituted with $C_1$-$C_6$-alkyl. For example, in some embodiments, $X^4$ is —N(CH$_3$)—. In those embodiments, the compound is encompassed by the following formula:

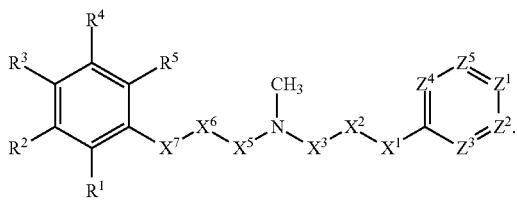

In some embodiments, $X^3$ is —C(O)—, and $X^4$ is —NH— substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. In some such embodiments, $X^3$ is —C(O)—, and $X^4$ is —NH—. In those embodiments, the compound is encompassed by the following formula:

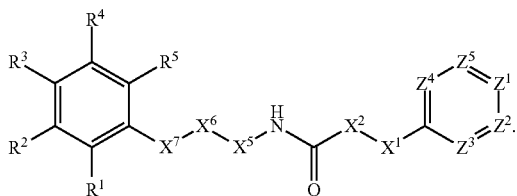

In other embodiments, $X^3$ is —C(O)—, and $X^4$ is —NH— substituted with $C_1$-$C_6$-alkyl. For example, in some such embodiments, $X^4$ is —N(CH$_3$)—. In those embodiments, the compound is encompassed by the following formula:

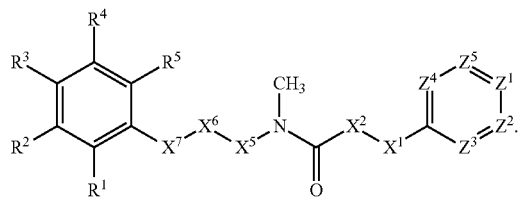

F. Preferred Embodiments of $X^5$ $X^5$ is selected from the group consisting of —O—, —CH$_2$—, —C(S)—, —C(O)—, —S(O)—, and —S(O)$_2$—. The —CH$_2$— is optionally substituted with up to two substituents independently selected from the group consisting of alkyl and carbocyclyl.

In some embodiments, $X^5$ is selected from the group consisting of —O—, —CH$_2$—, —C(S)—, —C(O)—, —S(O)—, and —S(O)$_2$—. The —CH$_2$— is optionally substituted with up to two substituents independently selected from the group consisting of $C_1$-$C_6$-alkyl and cycloalkyl (e.g., $C_3$-$C_6$-cycloalkyl, such as cyclopropyl).

In some embodiments, $X^5$ is —C(O)—. In those embodiments, the compound is encompassed by the following formula:

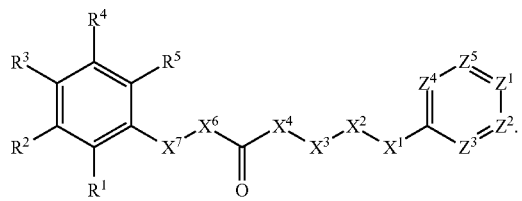

In other embodiments, $X^5$ is —C(S)—. In those embodiments, the compound is encompassed by the following formula:

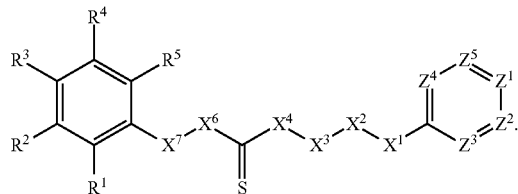

In still other embodiments, $X^5$ is —S(O)$_2$—. In those embodiments, the compound is encompassed by the following formula:

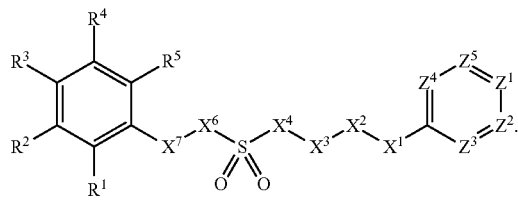

In still yet other embodiments, $X^5$ is —CH$_2$—. In such embodiments, the compound is encompassed by the following formula:

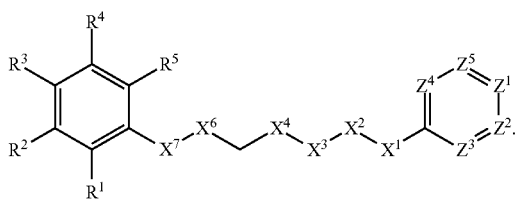

In some embodiments, $X^5$ is —C(O)—, and $X^4$ is —NH— substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. In some such embodiments, $X^5$ is —C(O)—, and $X^4$ is —NH—. In those embodiments, the compound is encompassed by the following formula:

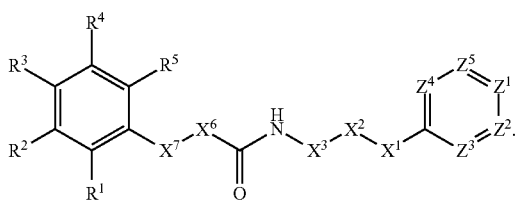

In other embodiments, $X^5$ is —C(O)—, and $X^4$ is —NH— substituted with $C_1$-$C_6$-alkyl. For example, in some such embodiments, $X^4$ is —N(CH$_3$)—. In those embodiments, the compound is encompassed by the following formula:

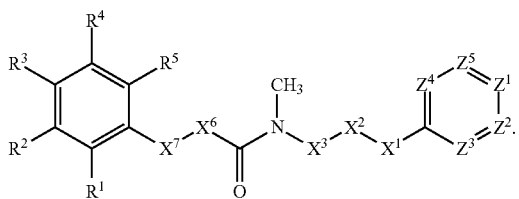

In general, no greater than one of $X^5$ and $X^3$ is optionally substituted —CH$_2$—.

G. Preferred Embodiments of $X^6$ $X^6$ is a linker. The linker is a hydrocarbon group, wherein: (a) the linker comprises one or more nitrogen atoms, and (b) one or more of the carbons in the hydrocarbon optionally are substituted with one or more substituents independently selected from the group consisting of oxo, halogen, hydroxy, and alkoxy. The linker comprises at least one chain of from 3 to 6 atoms that bridges $X^5$ to $X^7$. From 1 to 2 of the chain atoms are nitrogen. The linker has no chain of less than 3 atoms that bridges $X^5$ and $X^7$.

In some embodiments, the linker is a hydrocarbon group, except: (a) the linker comprises one or more nitrogen atoms, and (b) one or more of the carbons in the hydrocarbon optionally are substituted with one or more substituents independently selected from the group consisting of oxo, halogen, hydroxy, and $C_1$-$C_6$-alkoxy.

In some embodiments, the linker is a hydrocarbon group, except: (a) the linker comprises one or more nitrogen atoms, and (b) one or more of the carbons in the hydrocarbon optionally are substituted with oxo.

In some embodiments, the linker is a hydrocarbon group, except: (a) the linker comprises one or more nitrogen atoms, and (b) one carbon in the hydrocarbon is substituted with oxo.

In some embodiments, the linker is a hydrocarbon group, except for comprising one or more nitrogen atoms.

In some embodiments, the linker comprises no greater than one nitrogen atom.

In other embodiments, the linker comprises no greater and no less than two nitrogen atoms.

In some embodiments, the linker comprises at least one chain of from 3 to 5 atoms that bridges $X^5$ to $X^7$.

In some embodiments, the linker comprises at least one 3-atom chain that bridges $X^5$ to $X^7$.

In some embodiments, the linker comprises at least one 4-atom chain that bridges $X^5$ to $X^7$. In some such embodiments, the linker has no chain of less than 4 atoms that bridges $X^5$ to $X^7$.

In some embodiments, the linker comprises at least one 5-atom chain that bridges $X^5$ to $X^7$. In some such embodiments, the linker has no chain of less than 5 atoms that bridges $X^5$ to $X^7$.

In some embodiments, the linker comprises at least one 6-atom chain that bridges $X^5$ to $X^7$. In some such embodiments, the linker has no chain of less than 6 atoms that bridges $X^5$ to $X^7$.

In some embodiments, $X^6$ is selected from the group of linkers consisting of those shown in Table I:

TABLE I

Example of $X^6$ Linkers

TABLE I-continued

Example of $X^6$ Linkers

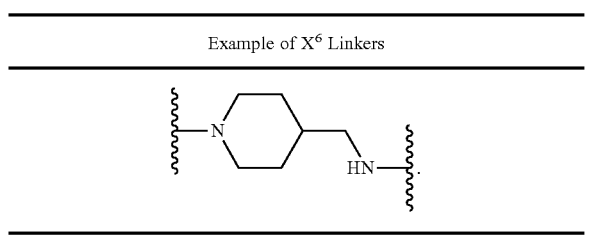

Any such group is optionally substituted with one or more substituents independently selected from the group consisting of halogen, $C_1$-$C_6$-alkyl, hydroxy, $C_1$-$C_6$-alkoxy, oxo, and thiocarbonyl.

In some embodiments, the linker comprises at least one 3-atom chain that bridges $X^5$ to $X^7$. To illustrate, the following are some of the structures from Table I that exemplify such linkers:

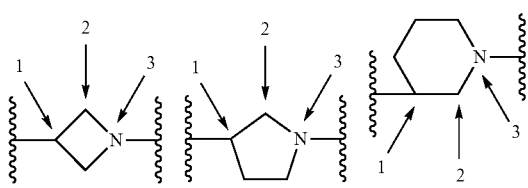

In some embodiments, the linker comprises at least one 4-atom chain that bridges $X^5$ to $X^7$. To illustrate, the following are some of the structures from Table I that exemplify such linkers:

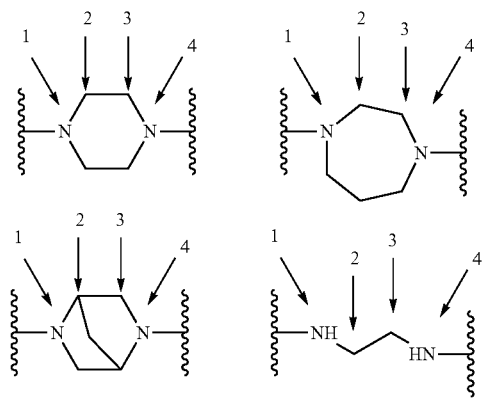 [SMILES: *N1CCN(*)CC1 ; *N1CCCN(*)CC1 ; *N1CC2CC1CN2* ; *NCCN*]

In some embodiments, the linker comprises at least one 5-atom chain that bridges $X^5$ to $X^7$. To illustrate, the following are some of the structures from Table I that exemplify such linkers:

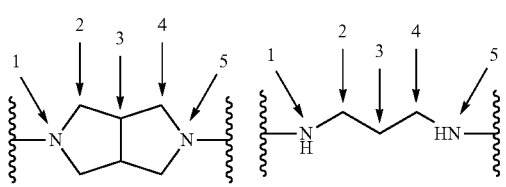

In some embodiments, the linker comprises at least one 6-atom chain that bridges $X^5$ to $X^7$. To illustrate, the following is a structure from Table I that exemplifies such a linker:

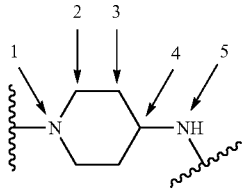

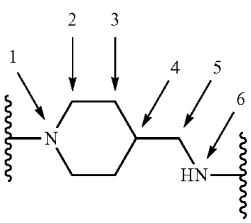 [SMILES: *NCC1CCN(*)CC1]

In some embodiments, the structures in Table I are not substituted with any $C_1$-$C_6$-alkyl or oxo.

In some embodiments, $X^6$ does not comprise a ring. In some such embodiments, $X^6$ is a linker selected from the group consisting of:

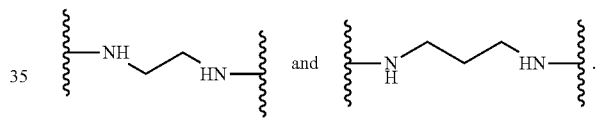

Any such group is optionally substituted with one or more substituents independently selected from the group consisting of $C_1$-$C_6$-alkyl and oxo.

In some embodiments, $X^6$ is one of the single- or double-ring structures in Table I. The ring(s) is/are optionally substituted with one or more substituents independently selected from the group consisting of halogen, hydroxy, $C_1$-$C_6$-alkyl, $C_1$-$C_6$-alkoxy, oxo, and thiocarbonyl.

In some embodiments, $X^6$ is one of the 4- to 7-member single ring structures in Table I. The ring is optionally substituted with one or more substituents independently selected from the group consisting of halogen, hydroxy, $C_1$-$C_6$-alkyl, $C_1$-$C_6$-alkoxy, oxo, and thiocarbonyl.

In some embodiments, $X^6$ is one of the 4- to 7-member single ring structures in Table I. The ring is optionally substituted with one or more substituents independently selected from the group consisting of halogen, hydroxy, $C_1$-$C_6$-alkyl, $C_1$-$C_6$-alkoxy, and oxo.

In some embodiments, $X^6$ is one of the 4- to 7-member single ring structures in Table I. The ring is optionally substituted with one or more substituents independently selected from the group consisting of $C_1$-$C_6$-alkyl and oxo.

In some embodiments, $X^6$ is:

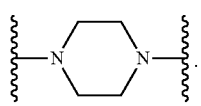

In those embodiments, the compound is encompassed by the following formula:

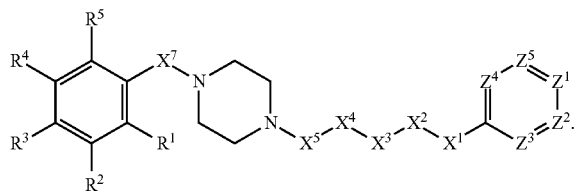

In some embodiments, $X^6$ is:

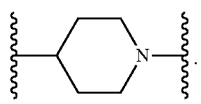 [SMILES: *C1CCN(*)CC1]

In such embodiments, the compound is encompassed by the following formula:

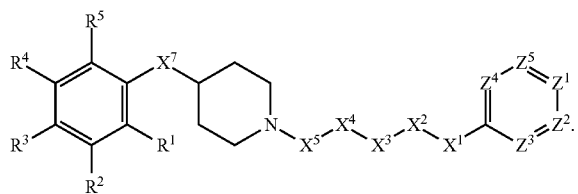

In some embodiments, $X^6$ is:

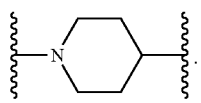 [SMILES: *C1CCN(*)CC1]

In such embodiments, the compound is encompassed by the following formula:

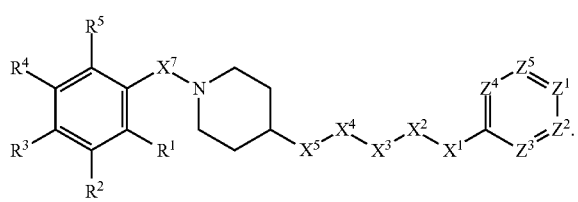

In some such embodiments, $X^5$ is —C(O)—, and the compound is encompassed by the following formula:

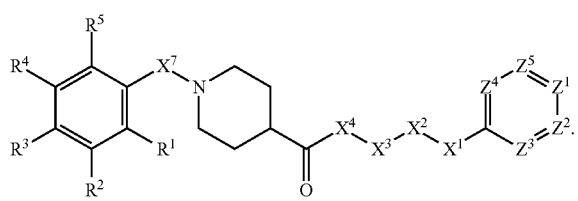

In other embodiments, $X^5$ is —C(O)—, $X^4$ is —N(H)—, and the compound is encompassed by the following formula:

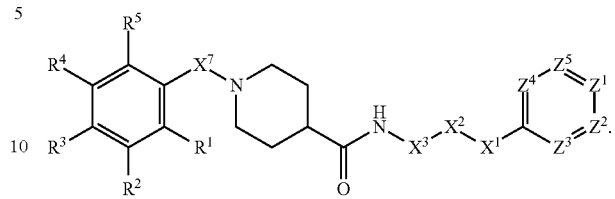

In still other embodiments, $X^5$ is —C(O)—, $X^4$ is —N(CH$_3$)—, and the compound is encompassed by the following formula:

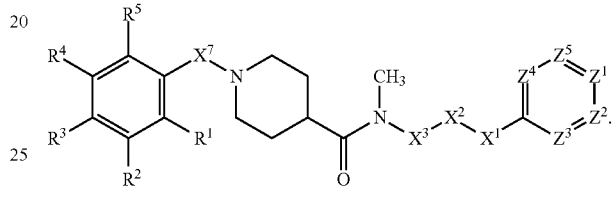

In some embodiments, $X^6$ is:

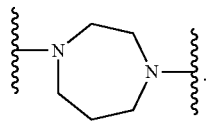

In such embodiments, the compound is encompassed by the following formula:

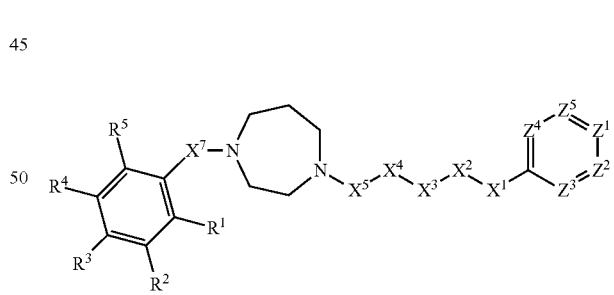

In some embodiments, $X^6$ is:

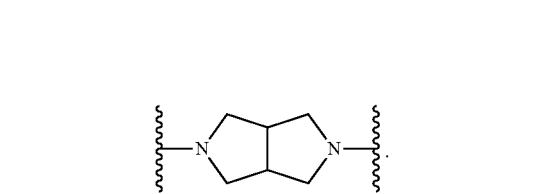 [SMILES: *N1CC2CN(*)CC2C1]

In such embodiments, the compound is encompassed by the following formula:

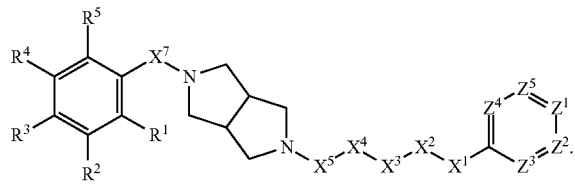

In some embodiments, $X^6$ is:

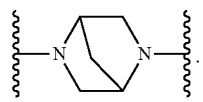

In such embodiments, the compound is encompassed by the following formula:

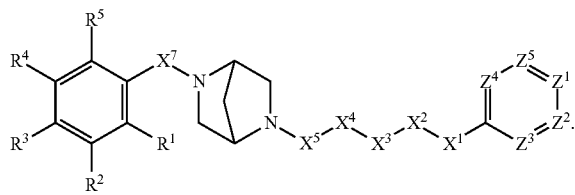

In some embodiments, $X^6$ is:

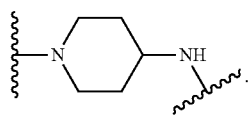

In such embodiments, the compound is encompassed by the following formula:

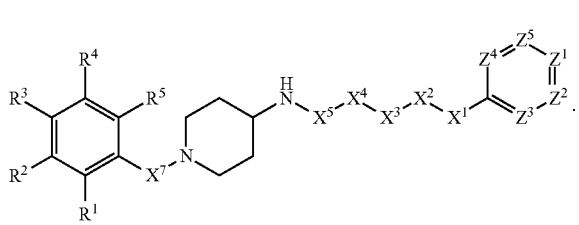

In some embodiments, $X^6$ is:

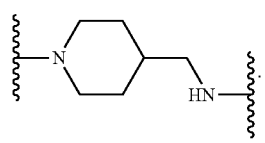 [SMILES: *NCC1CCN(*)CC1]

In such embodiments, the compound is encompassed by the following formula:

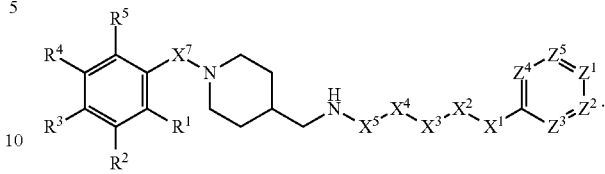

In some embodiments, one or more carbon atoms in the linker are substituted with one or two substituents independently selected from the group consisting of halogen, hydroxy, $C_1$-$C_6$-alkyl, $C_1$-$C_6$-alkoxy, oxo, and thiocarbonyl.

In some embodiments, one or more carbon atoms in the linker are substituted with one or two substituents independently selected from the group consisting of halogen, hydroxy, $C_1$-$C_6$-alkyl, $C_1$-$C_6$-alkoxy, and oxo.

In some embodiments, $X^6$ is one of the single- or double-ring structures in Table I, and one or two of the ring atoms in the ring structure are substituted with a substituent independently selected from the group consisting of methyl and oxo. To illustrate, in some embodiments, the a ring atom is substituted with an oxo substituent. The linker in such an instance may be, for example:

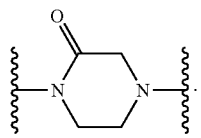 [SMILES: *N1CCN(*)C(=O)C1]

Here, the compound is encompassed by the following formula:

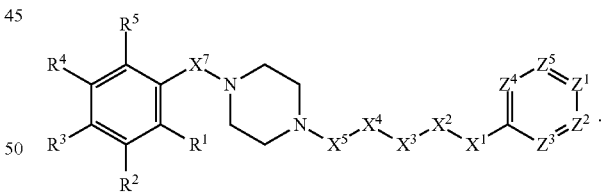

In other embodiments, for example, one or two of the ring atoms are substituted with methyl. To illustrate, the linker in such an instance may be, for example:

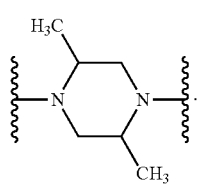 [SMILES: *N1CC(C)N(*)CC1C]

Here, the compound is encompassed by the following formula:

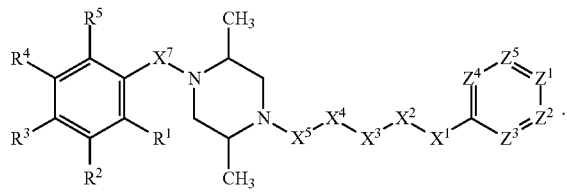

To further illustrate, the linker may alternatively be, for example:

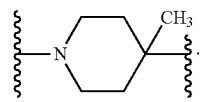

Here, the compound is encompassed by the following formula:

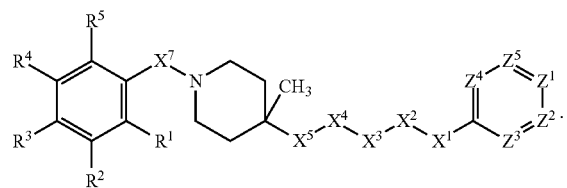

In some such embodiments, for example, $X^5$ is —C(O)—. In those embodiments, the compound is encompassed by the following formula:

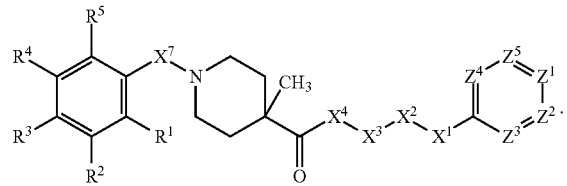

H. Preferred Embodiments of $X^7$ $X^7$ is selected from the group consisting of a bond, —O—, —C(O)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$—. The —NH— is optionally substituted with alkyl. And the —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$— are optionally substituted with one or more independently selected alkyl.

In some embodiments, $X^7$ is selected from the group consisting of a bond, —O—, —C(O)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$—. The —NH— is optionally substituted with $C_1$-$C_6$-alkyl. And the —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$— are optionally substituted with one or more independently selected $C_1$-$C_6$-alkyl.

In some embodiments, $X^7$ is a bond. In such embodiments, the compound is encompassed by the following formula:

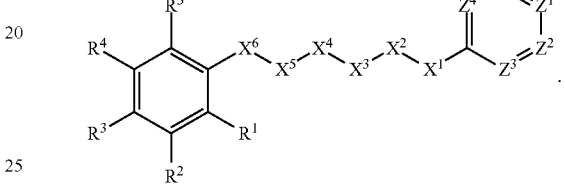

I. Preferred Embodiments of $Z^1$, $Z^2$, $Z^3$, $Z^4$, and $Z^5$ $Z^1$ is selected from the group consisting of N and CH. The CH is substituted with a substituent selected from the group consisting of halogen, nitro, cyano, aminosulfonyl, alkyl, alkoxy, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl. The alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl. The aminosulfonyl is optionally substituted with up to two independently selected alkyl.

In some embodiments, $Z^1$ is selected from the group consisting of N and CH. The CH is substituted with a substituent selected from the group consisting of halogen, nitro, cyano, aminosulfonyl, $C_1$-$C_6$-alkyl, $C_1$-$C_6$-alkoxy, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, aryl, arylsulfanyl, arylsulfinyl, arylsulfonyl, heteroaryl, heteroarylsulfanyl, heteroarylsulfinyl, and heteroarylsulfonyl. The $C_1$-$C_6$-alkyl, $C_1$-$C_6$-alkoxy, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, $C_1$-$C_6$-alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and $C_1$-$C_6$-alkyl. The aminosulfonyl is optionally substituted with up to two independently selected $C_1$-$C_6$-alkyl. In some such embodiments, each aryl is phenyl, and each heteroaryl is a 5- to 6-member heteroaryl.

In some embodiments, $Z^1$ is N. Such embodiments are encompassed by the following structure:

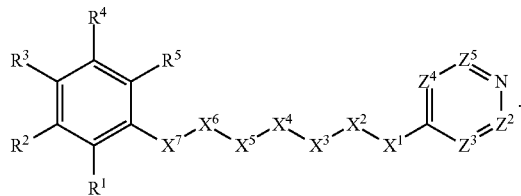

In some embodiments, $Z^1$ is CH substituted with a substituent selected from the group consisting of halogen, nitro, cyano, $C_1$-$C_6$-alkoxy, and $C_1$-$C_6$-alkylsulfanyl. The $C_1$-$C_6$-alkoxy and $C_1$-$C_6$-alkylsulfanyl are optionally substituted with one or more independently selected halogen.

In some embodiments, $Z^1$ is CH substituted with an electron-withdrawing substituent. Such substituents include, for example, halogen, nitro, cyano, halo-$C_1$-$C_6$-alkyl, halo-$C_1$-$C_6$-alkoxy, and halo-$C_1$-$C_6$-alkylsulfanyl.

In some embodiments, $Z^1$ is CH substituted with a halogen. For example, in some such embodiments, $Z^1$ is CH substituted with chloro. These embodiments are encompassed by the following structure:

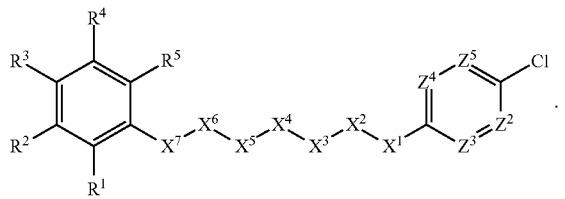

In some embodiments, $Z^1$ is CH substituted with nitro. Such embodiments are encompassed by the following structure:

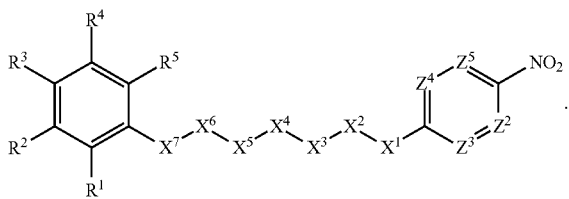

In some embodiments, $Z^1$ is CH substituted with cyano. Such embodiments are encompassed by the following structure:

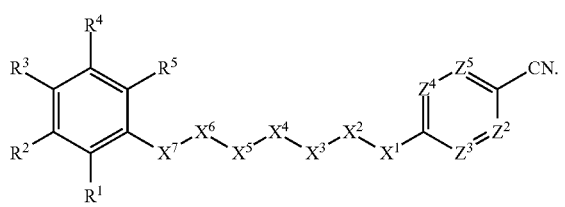

In some embodiments, $Z^1$ is CH substituted with halo-$C_1$-$C_6$-alkoxy. For example, in some such embodiments, $Z^1$ is CH substituted with fluoro-$C_1$-$C_6$-alkoxy. To illustrate, $Z^1$ can be, for example, CH substituted trifluoromethoxy such that the compound is encompassed by the following structure:

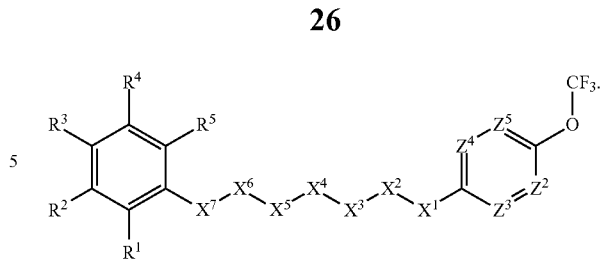

In some embodiments, $Z^1$ is CH substituted with halo-$C_1$-$C_6$-alkylsulfanyl. For example, in some such embodiments, $Z^1$ is CH substituted with fluoro-$C_1$-$C_6$-alkylsulfanyl. To illustrate, $Z^1$ can be, for example, CH substituted trifluoromethylsulfanyl such that the compound is encompassed by the following structure:

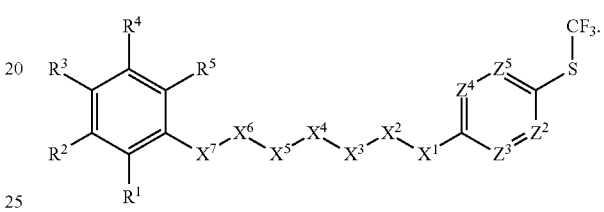

$Z^2$ is selected from the group consisting of N and CH. The CH is optionally substituted with a substituent selected from the group consisting of cyano, halogen, nitro, alkyl, alkoxy, haloalkyl, and haloalkylsulfanyl.

In some embodiments, $Z^2$ is selected from the group consisting of N and CH. The CH is optionally substituted with a substituent selected from the group consisting of cyano, halogen, nitro, $C_1$-$C_6$-alkyl, $C_1$-$C_6$-alkoxy, halo-$C_1$-$C_6$-alkyl, and halo-$C_1$-$C_6$-alkylsulfanyl.

In some embodiments, $Z^2$ is N. Such embodiments are encompassed by the following structure:

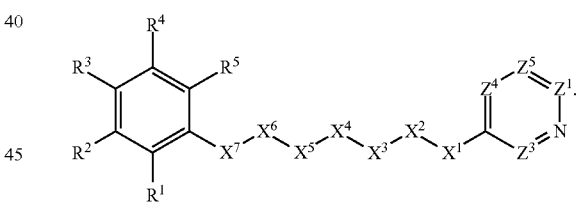

In some embodiments, $Z^2$ is CH substituted with a substituent selected from the group consisting of cyano, halogen, nitro, $C_1$-$C_6$-alkyl, $C_1$-$C_6$-alkoxy, halo-$C_1$-$C_6$-alkyl, and halo-$C_1$-$C_6$-alkylsulfanyl.

In some embodiments, $Z^2$ is CH substituted with halo-$C_1$-$C_6$-alkyl. In some such embodiments, for example, $Z^2$ is CH substituted with trifluoromethyl. Such embodiments are encompassed by the following structure:

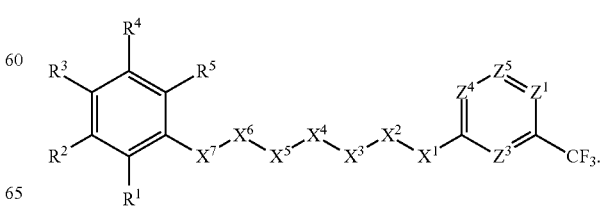

Each of $Z^3$, $Z^4$, and $Z^5$ is independently selected from the group consisting of N and CH. The CH is optionally substituted with a substituent selected from the group consisting of halogen, cyano, nitro, alkyl, alkoxy, alkylsulfanyl, haloalkyl, haloalkoxy, and haloalkylsulfanyl.

Each of $Z^3$, $Z^4$, and $Z^5$ is independently selected from the group consisting of N and CH. The CH is optionally substituted with a substituent selected from the group consisting of halogen, cyano, nitro, $C_1$-$C_6$-alkyl, $C_1$-$C_6$-alkoxy, $C_1$-$C_6$-alkylsulfanyl, halo-$C_1$-$C_6$-alkyl, halo-$C_1$-$C_6$-alkoxy, and halo-$C_1$-$C_6$-alkylsulfanyl.

In some embodiments, one of $Z^3$, $Z^4$, and $Z^5$ is CH.

In some embodiments, two of $Z^3$, $Z^4$, and $Z^5$ are each independently selected from the group consisting of N and CH optionally substituted with $C_1$-$C_6$-alkyl.

In some embodiments, one of $Z^3$, $Z^4$, and $Z^5$ is CH; and the remaining two of $Z^3$, $Z^4$, and $Z^5$ are each independently selected from the group consisting of N and CH optionally substituted with $C_1$-$C_6$-alkyl.

In some embodiments, one of $Z^3$, $Z^4$, and $Z^5$ is CH; and the remaining two of $Z^3$, $Z^4$, and $Z^5$ are each independently selected from the group consisting of N, CH, and $C(CH_3)$.

In some embodiments, two of $Z^3$, $Z^4$, and $Z^5$ are each CH.

In some embodiments, all of $Z^3$, $Z^4$, and $Z^5$ are each CH. Such embodiments are encompassed by the following structure:

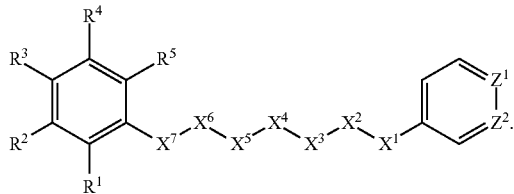

In some embodiments, two of $Z^1$, $Z^2$, $Z^3$, $Z^4$, and $Z^5$ are each N. In other embodiments, only one of $Z^1$, $Z^2$, $Z^3$, $Z^4$, and $Z^5$ is N. And, in yet other embodiments, none of $Z^1$, $Z^2$, $Z^3$, $Z^4$, and $Z^5$ are N.

J. Examples of Various Specific Preferred Embodiments

In some embodiments of this invention, the compound is defined as corresponding in structure to the following formula:

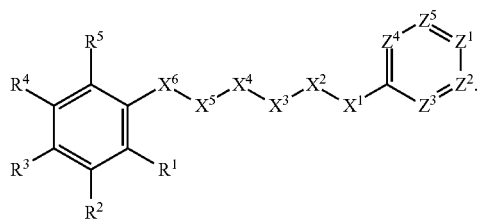

In some such embodiments:
Two of $R^1$, $R^2$, $R^3$, $R^4$, and $R^5$ are each hydrogen. The remaining three of $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen and halo-$C_1$-$C_6$-alkyl.

$X^1$ is selected from the group consisting of —O— and —NH—. The —NH— is optionally substituted with $C_1$-$C_6$-alkyl.

$X^2$ is selected from the group consisting of cyclobutyl, cyclopentyl, and cyclohexyl.

$X^3$ is selected from the group consisting of —$CH_2$—, —O—, and —C(O)—.

$X^4$ is selected from the group consisting of —$CH_2$— and —NH—. The —$CH_2$— is optionally substituted with up to two independently selected $C_1$-$C_6$-alkyl. The —NH— is optionally substituted with $C_1$-$C_6$-alkyl.

$X^5$ is selected from the group consisting of —$CH_2$—, —C(S)—, —C(O)—, and —$S(O)_2$—.

$X^6$ is selected from the group of linkers consisting of:

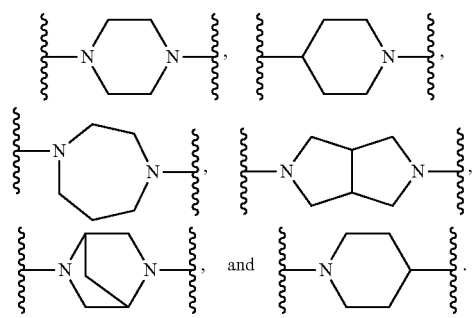

Here, any such group is optionally substituted with up to two substituents independently selected from the group consisting of $C_1$-$C_6$-alkyl and oxo.

$Z^1$ is CH substituted with a substituent selected from the group consisting of halogen, nitro, cyano, $C_1$-$C_6$-alkoxy, and $C_1$-$C_6$-alkylsulfanyl. The $C_1$-$C_6$-alkoxy and $C_1$-$C_6$-alkylsulfanyl are optionally substituted with one or more independently selected halogen.

$Z^2$ is CH optionally substituted with halo-$C_1$-$C_6$-alkyl.

One of $Z^3$, $Z^4$, and $Z^5$ is CH. The remaining two of $Z^3$, $Z^4$, and $Z^5$ are independently selected from the group consisting of N and CH, wherein the CH is optionally substituted with $C_1$-$C_6$-alkyl.

Compounds encompassed by these embodiments include, for example:

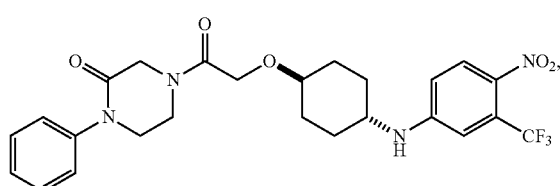

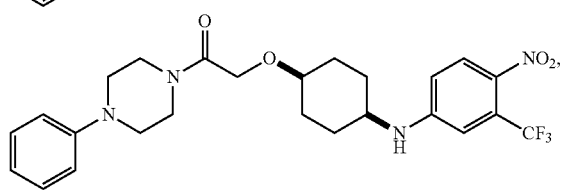

-continued
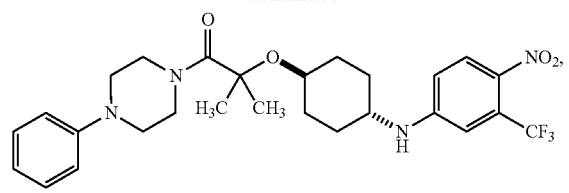
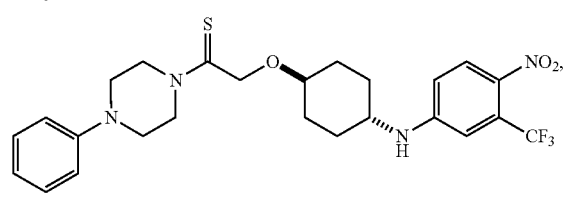
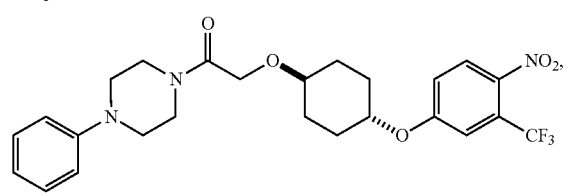
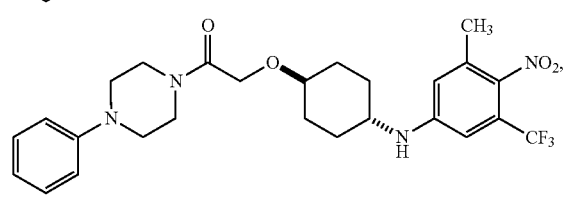
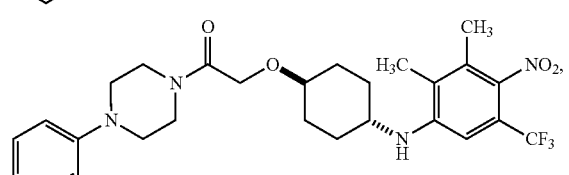
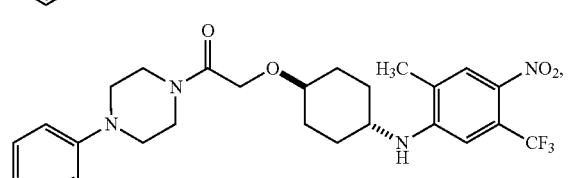
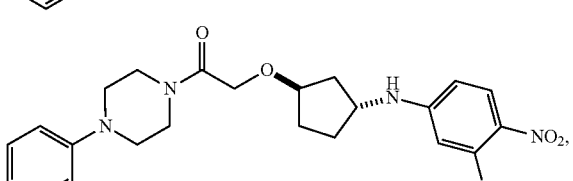
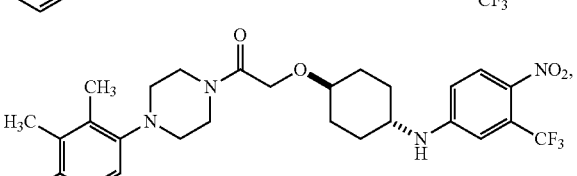
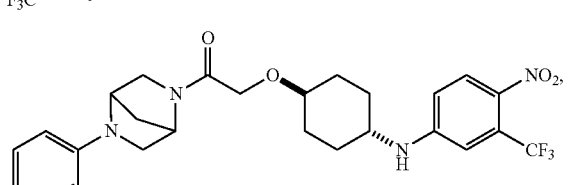
-continued
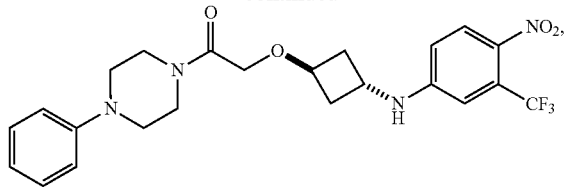
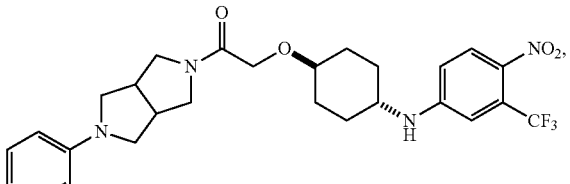
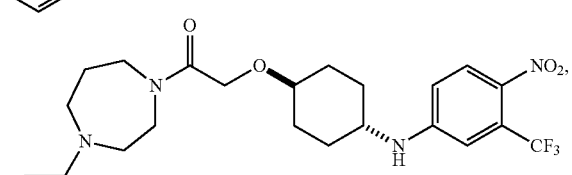
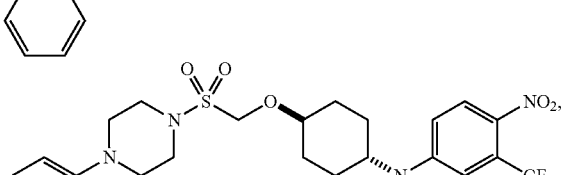
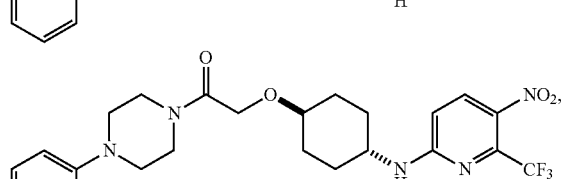
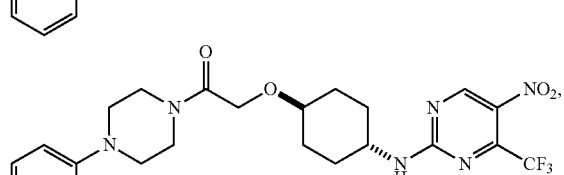
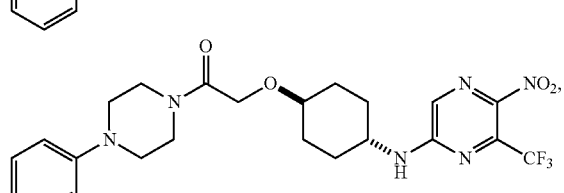
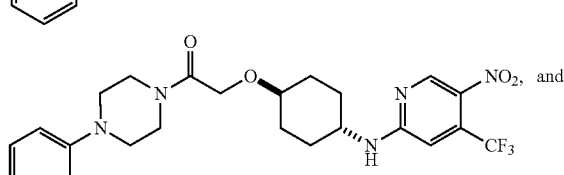
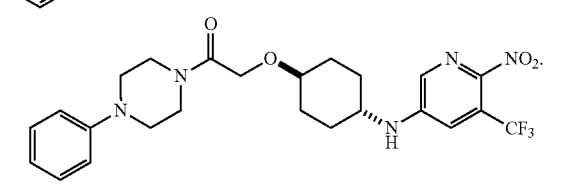

In some embodiments of this invention, the compound is defined as corresponding in structure to the following formula:

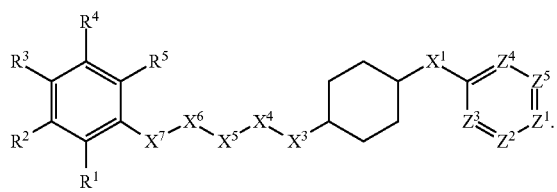

In some such embodiments:

- Two of $R^1$, $R^2$, $R^3$, $R^4$, and $R^5$ are each hydrogen. The remaining three of $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen and halo-$C_1$-$C_6$-alkyl.
- $X^1$ is —NH— optionally substituted with $C_1$-$C_6$-alkyl.
- $X^3$ is selected from the group consisting of —$CH_2$—, —O—, and —C(O)—.
- $X^4$ is selected from the group consisting of —$CH_2$— and —NH—.
- The —$CH_2$— is optionally substituted with up to two independently selected $C_1$-$C_6$-alkyl. The —NH— is optionally substituted with $C_1$-$C_6$-alkyl.
- $X^5$ is selected from the group consisting of —$CH_2$— and —C(O)—.
- $X^6$ is selected from the group of linkers consisting of:

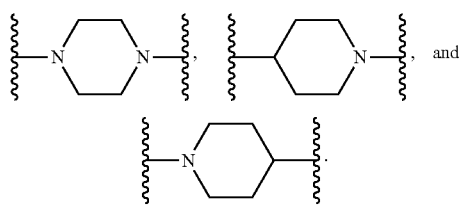

Any such group is optionally substituted with up to two substituents independently selected from the group consisting of $C_1$-$C_6$-alkyl and oxo.
- $Z^1$ is CH substituted with a substituent selected from the group consisting of halogen, nitro, cyano, $C_1$-$C_6$-alkoxy, and $C_1$-$C_6$-alkylsulfanyl. The $C_1$-$C_6$-alkoxy and $C_1$-$C_6$-alkylsulfanyl are optionally substituted with one or more independently selected halogen.
- $Z^2$ is CH optionally substituted with halo-$C_1$-$C_6$-alkyl.
- $Z^3$, $Z^4$, and $Z^5$ are each CH.

In some of these embodiments, $X^7$ is a bond such that the compound corresponds in structure to the following formula:

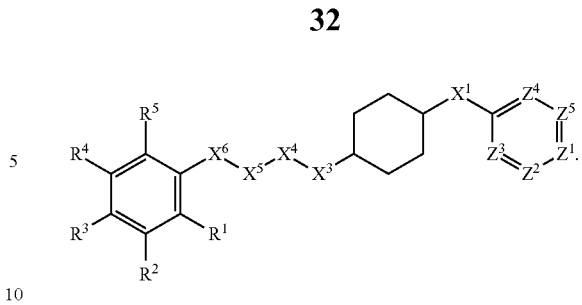

Compounds encompassed by these embodiments include, for example:

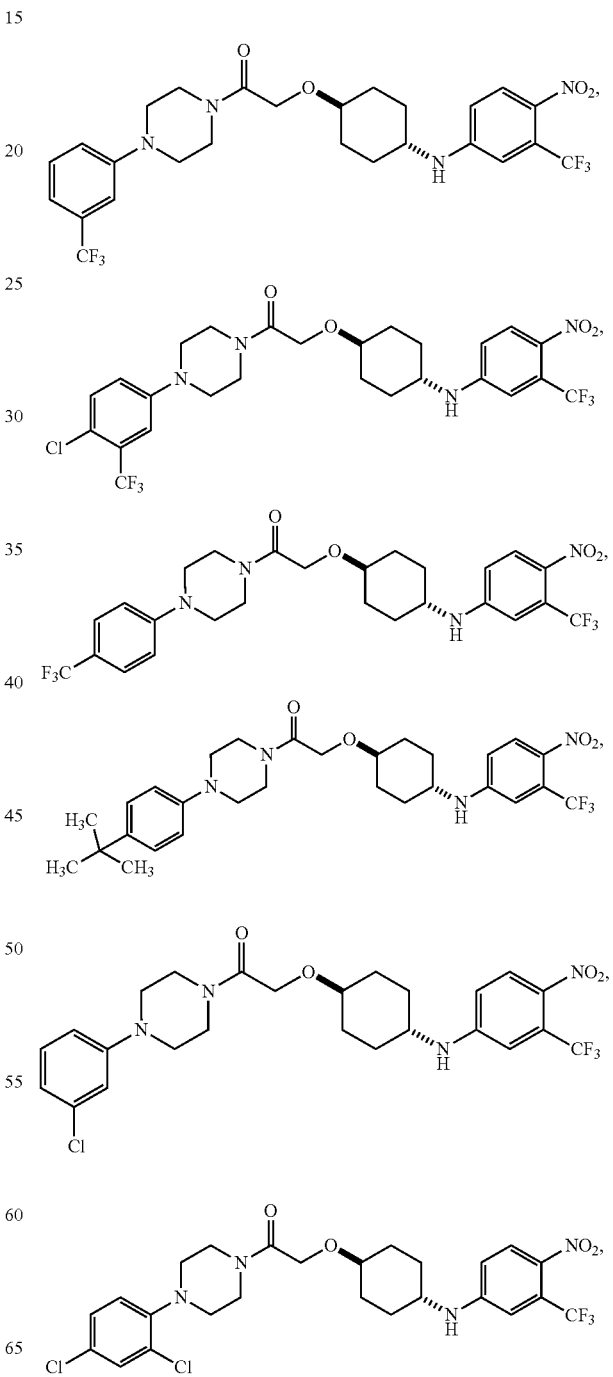

33
-continued
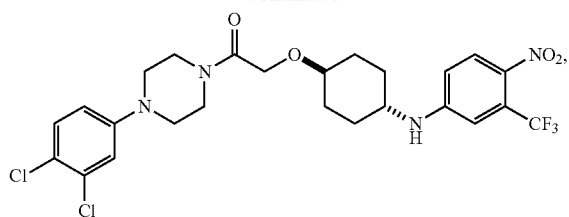
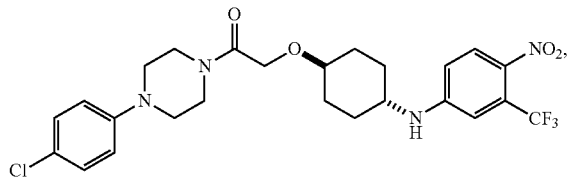
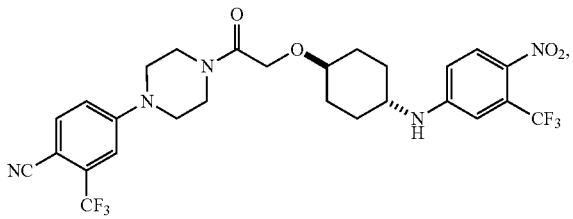
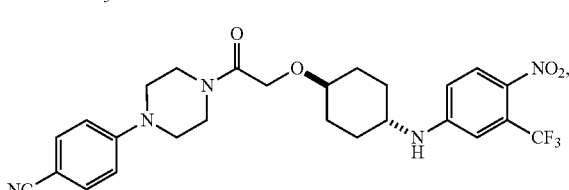
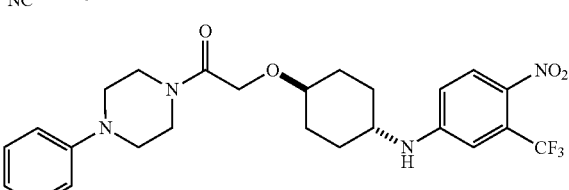
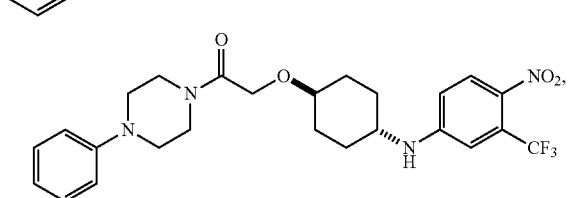
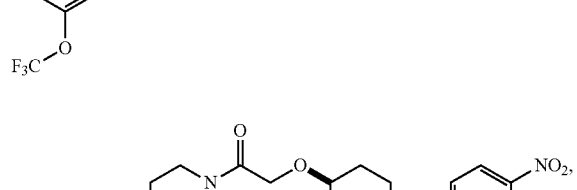
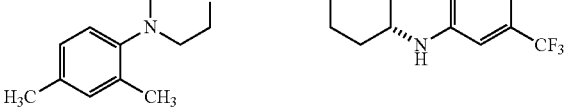
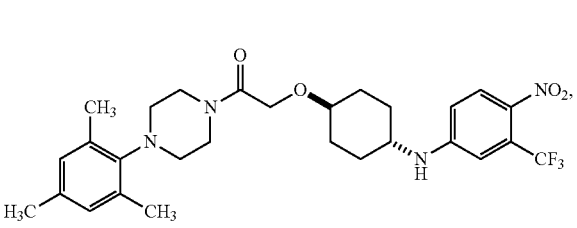
34
-continued
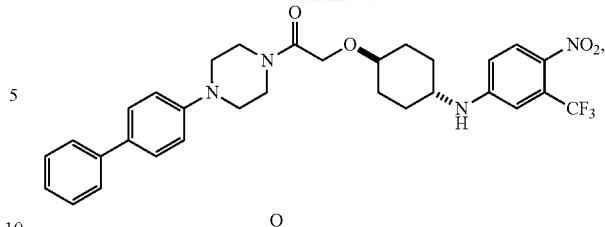
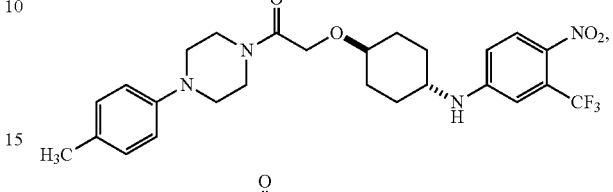
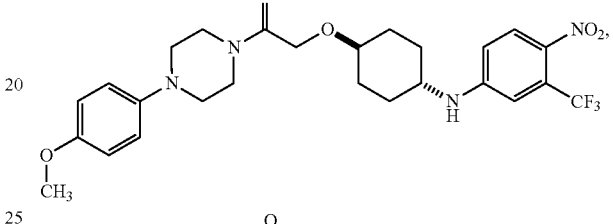
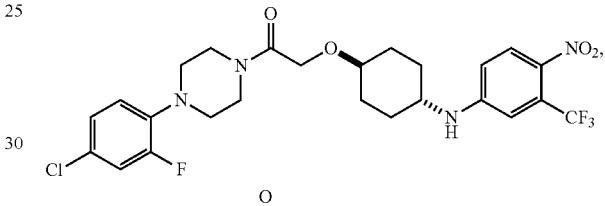
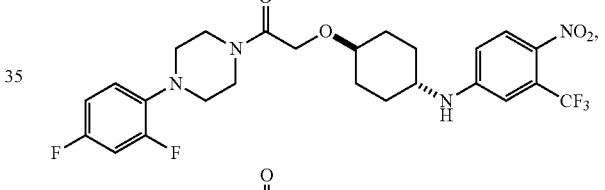
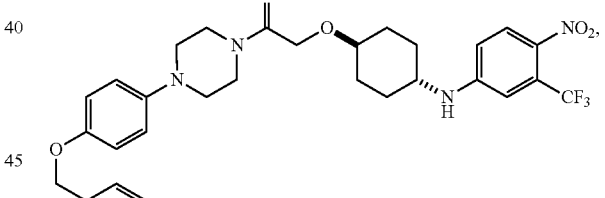
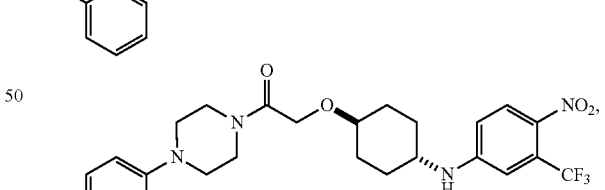
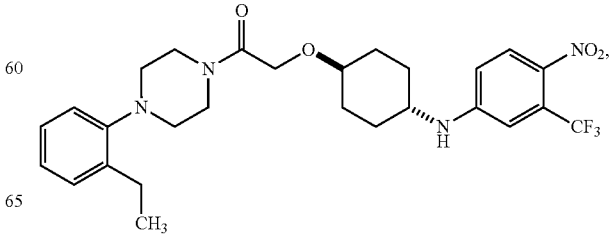

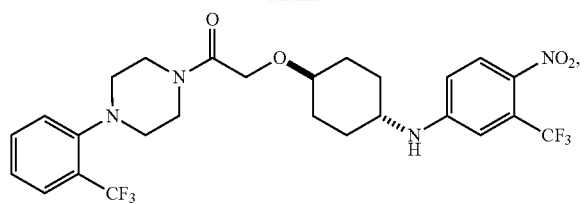
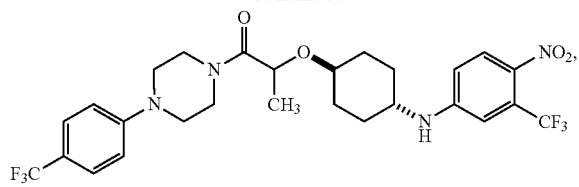
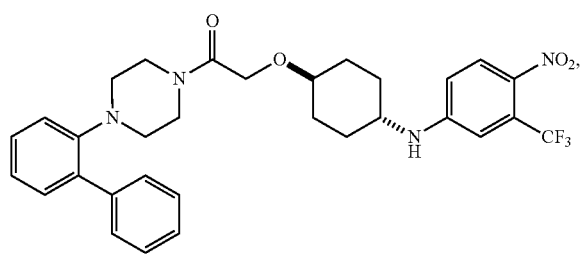
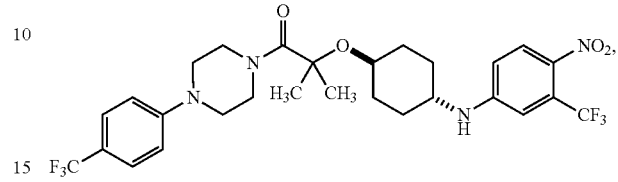
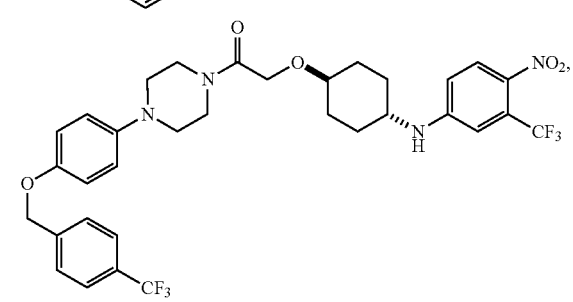
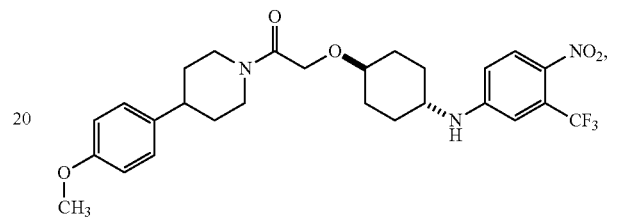
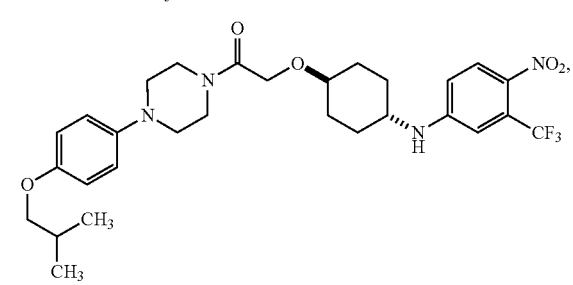
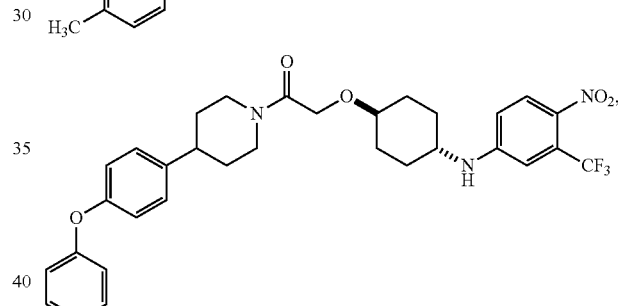
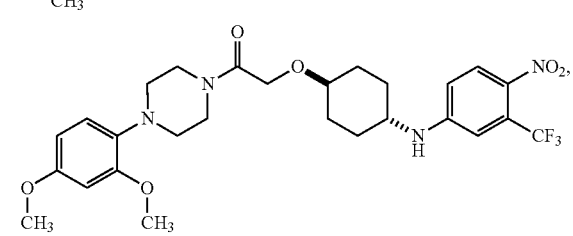
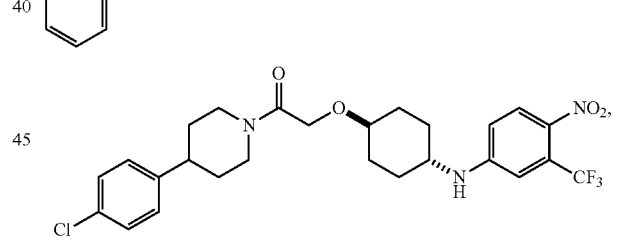
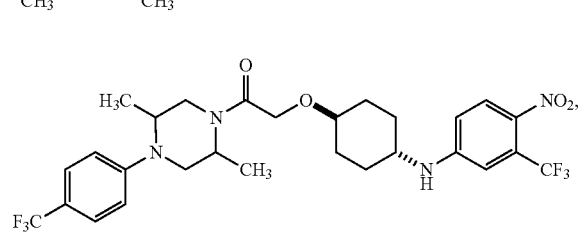
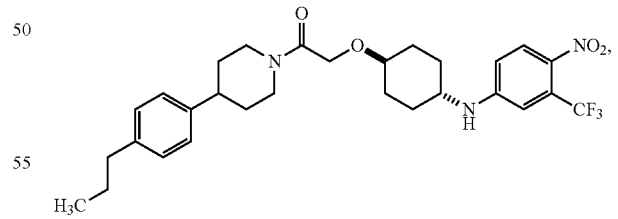
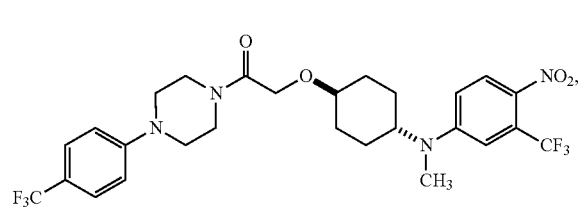
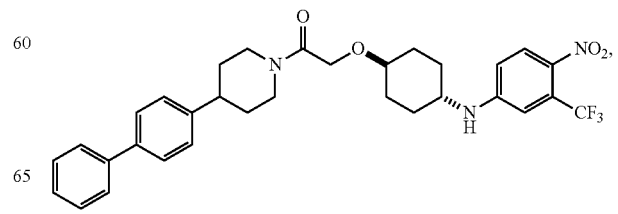

-continued
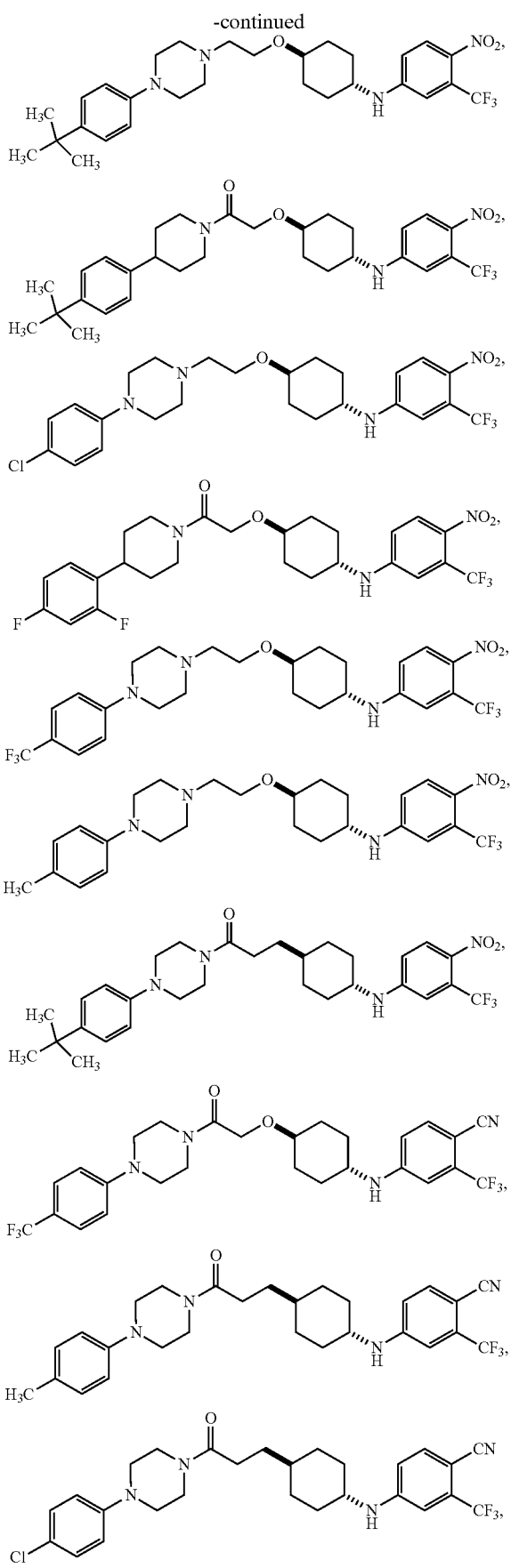
-continued
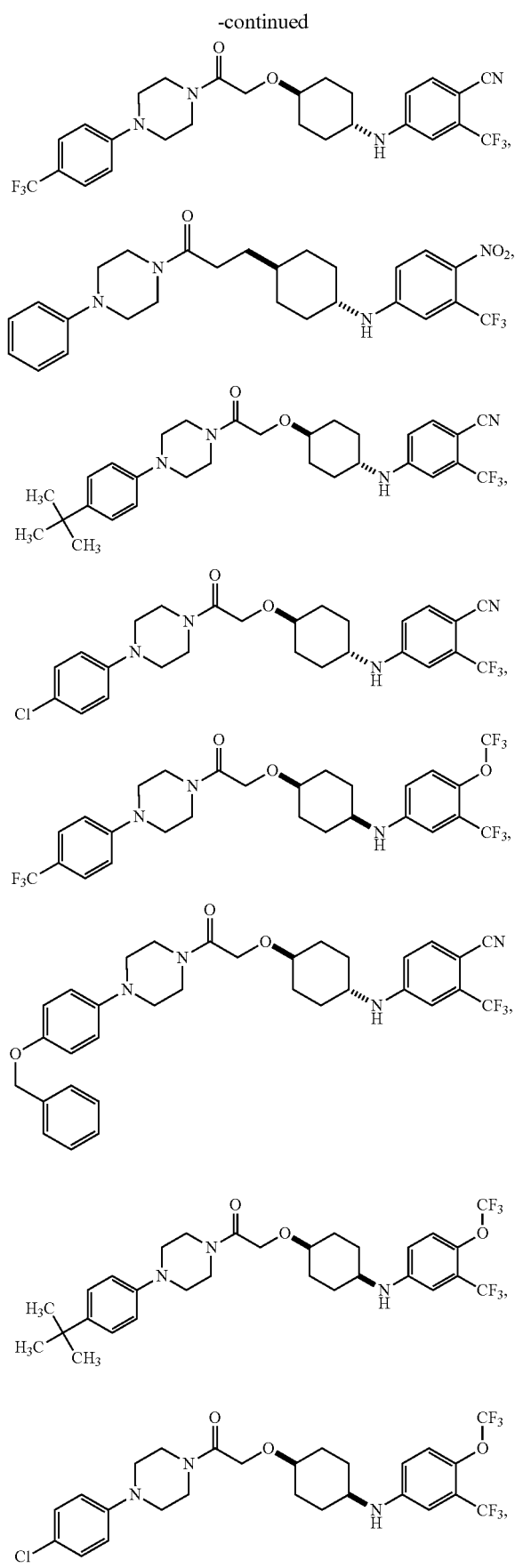

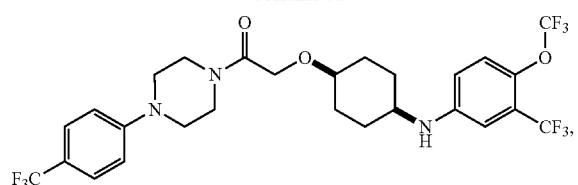
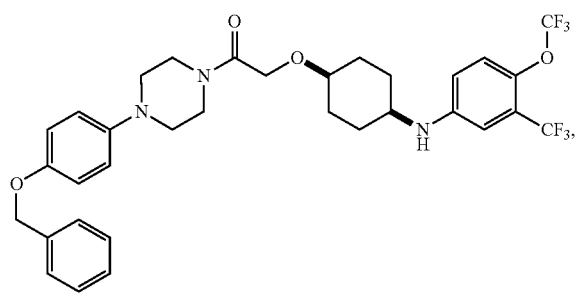
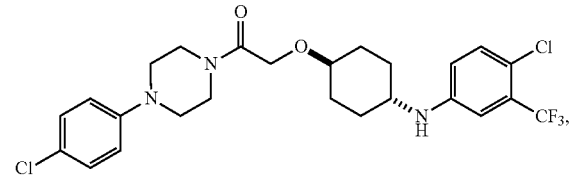
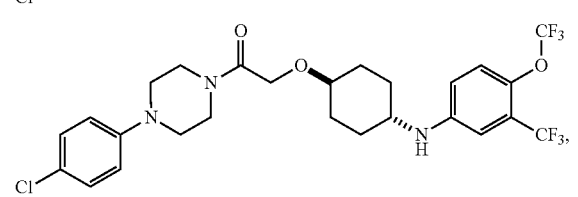
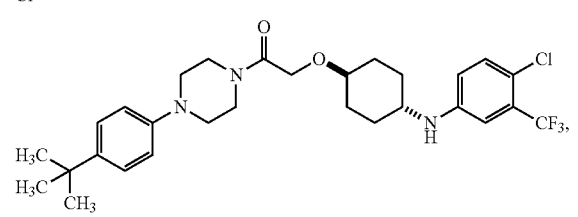
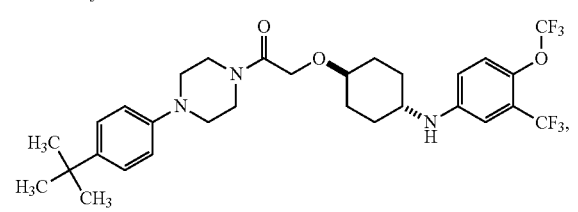
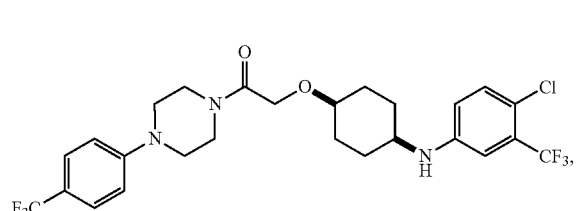
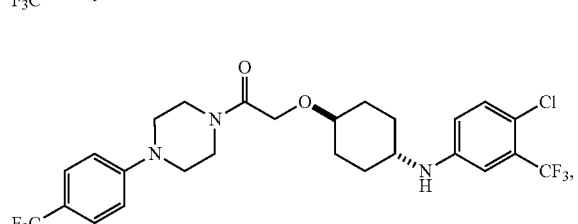
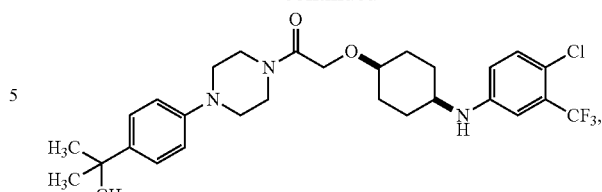
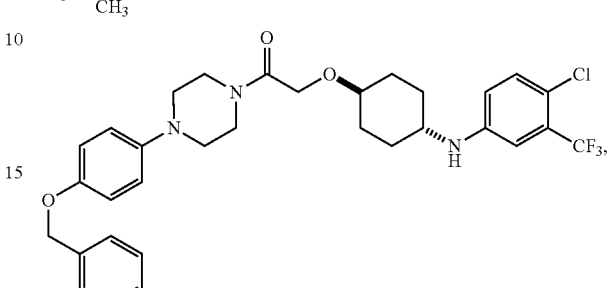
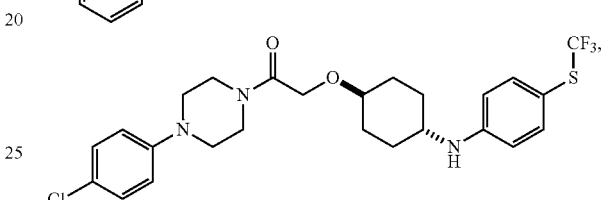
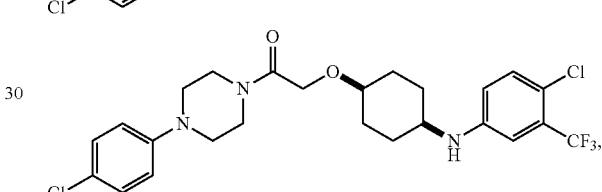
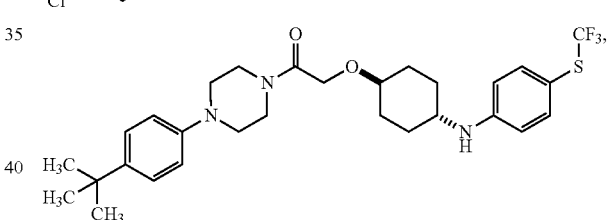
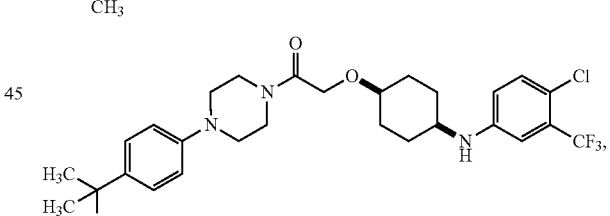
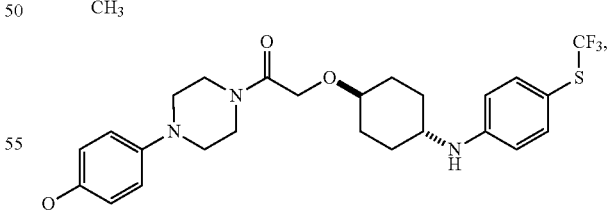
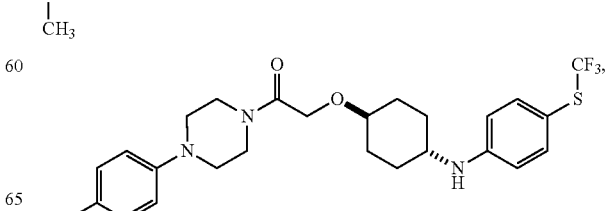

In some embodiments of this invention, the compound is defined as corresponding in structure to the following formula:

In some such embodiments:
Three of $R^1$, $R^2$, $R^3$, $R^4$, and $R^5$ are each independently selected from the group consisting of hydrogen, chloro, fluoro, cyano, nitro, methyl, tert-butyl, n-propyl, trifluoromethyl, ethyl, methoxy, ethoxy, trifluoromethoxy, trifluoromethylsulfanyl, iso-butoxy, phenyl, phenoxy, benzyloxy, and 4-trifluoromethylbenzyloxy. The remaining two of $R^1$, $R^2$, $R^3$, $R^4$, and $R^5$ are each hydrogen.
$X^1$ is selected from the group consisting of —O—, —NH—, and —N(CH$_3$)—.
$X^2$ is selected from the group consisting of cyclobutyl, cyclopentyl, and cyclohexyl.
$X^3$ is selected from the group consisting of —CH$_2$—, —O—, and —C(O)—.
$X^4$ is selected from the group consisting of —CH$_2$—, —C(H)(CH$_3$)—, —C(CH$_3$)$_2$—, —NH—, and —N(CH$_3$)—.
$X^5$ is selected from the group consisting of —CH$_2$—, —C(S)—, —C(O)—, and —S(O)$_2$—.
$X^6$ is selected from the group of linkers consisting of:

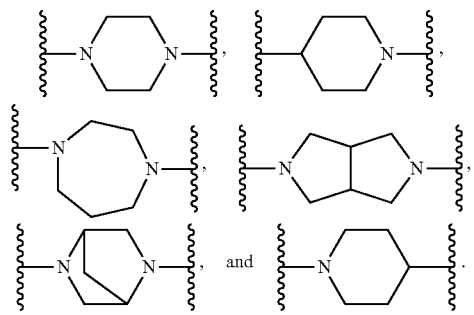

Any such group is optionally substituted with up to two substituents independently selected from the group consisting of methyl and oxo.
$Z^1$ is CH substituted with a substituent selected from the group consisting of chloro, nitro, cyano, trifluoromethoxy, and trifluoromethylsulfanyl.
$Z^2$ is CH optionally substituted with trifluoromethyl.
Two of $Z^3$, $Z^4$, and $Z^5$ are independently selected from the group consisting of N, CH, and C(CH$_3$). The remaining one of $Z^3$, $Z^4$, and $Z^5$ is CH.

In some embodiments of this invention, the compound is defined as corresponding in structure to the following formula:

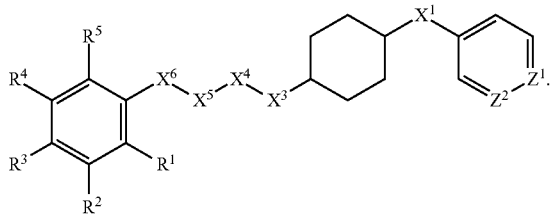

In some such embodiments:
Three of $R^1$, $R^2$, $R^3$, $R^4$, and $R^5$ are each independently selected from the group consisting of hydrogen, chloro, fluoro, cyano, nitro, methyl, tert-butyl, n-propyl, trifluoromethyl, ethyl, methoxy, ethoxy, trifluoromethoxy, trifluoromethylsulfanyl, iso-butoxy, phenyl, phenoxy, benzyloxy, and 4-trifluoromethylbenzyloxy. The remaining two of $R^1$, $R^2$, $R^3$, $R^4$, and $R^5$ are each hydrogen.
$X^1$ is selected from the group consisting of —NH— and —N(CH$_3$)—.
$X^3$ is selected from the group consisting of —CH$_2$—, —O—, and —C(O)—.
$X^4$ is selected from the group consisting of —CH$_2$, —C(H)(CH$_3$)—, —C(CH$_3$)$_2$—, —NH—, and —N(CH$_3$)—.
$X^5$ is selected from the group consisting of —CH$_2$— and —C(O)—.
$X^6$ is selected from the group of linkers consisting of:

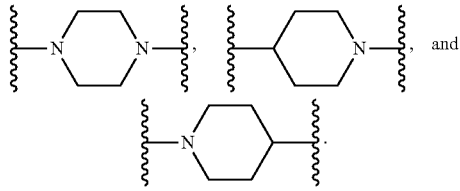

Any such group is optionally substituted with up to two methyl groups.
$Z^1$ is CH substituted with a substituent selected from the group consisting of chloro, nitro, cyano, trifluoromethoxy, and trifluoromethylsulfanyl.
$Z^2$ is CH optionally substituted with trifluoromethyl.

In some embodiments of this invention, the compound is defined as corresponding in structure to a formula selected from the group consisting of:

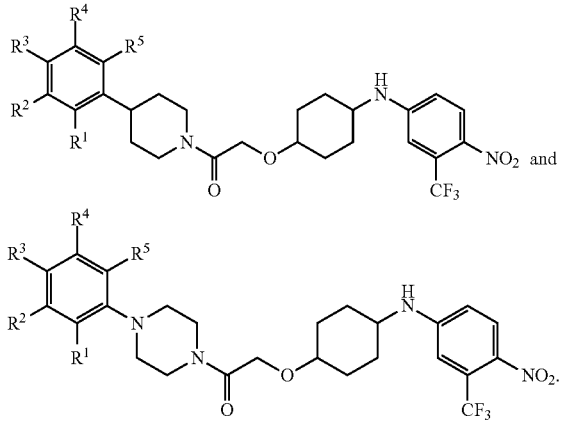

In some such embodiments:
$R^3$ is selected from the group consisting of halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy.
At least two of $R^1$, $R^2$, $R^4$, and $R^5$ are each hydrogen. The remaining two of $R^1$, $R^2$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy.

In some embodiments of this invention, the compound is defined as corresponding in structure to the following formula:

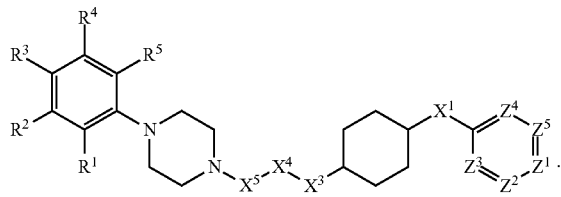

In some embodiments of this invention, the compound is defined as corresponding in structure to the following formula:

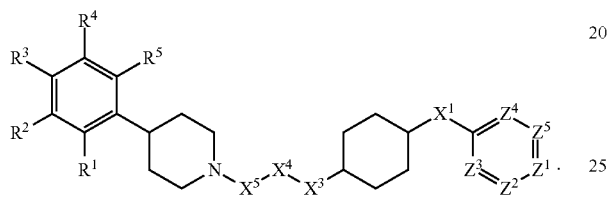

In some embodiments of this invention, the compound corresponds in structure to the following formula:

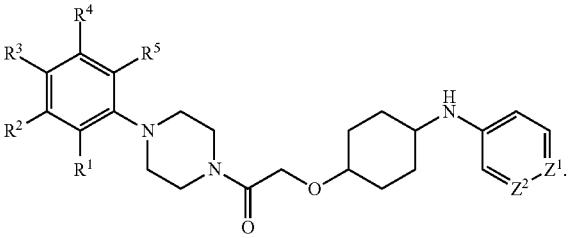

In some embodiments of this invention, the compound corresponds in structure to the following formula:

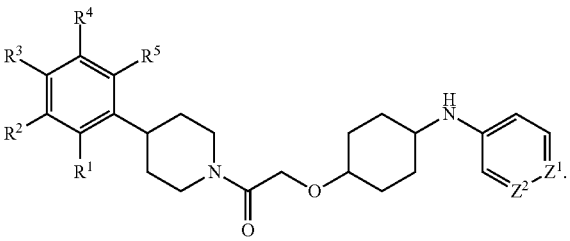

In some embodiments, the compound is defined as corresponding in structure to the following formula:

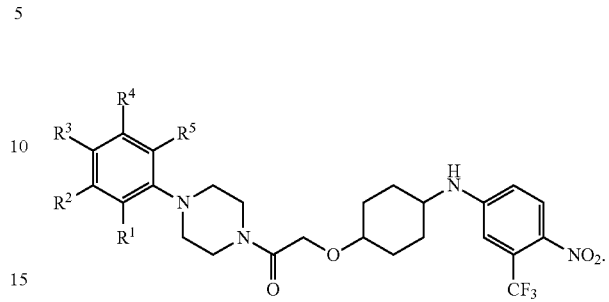

In some embodiments, the compound is defined as corresponding in structure to one of the following formulas:

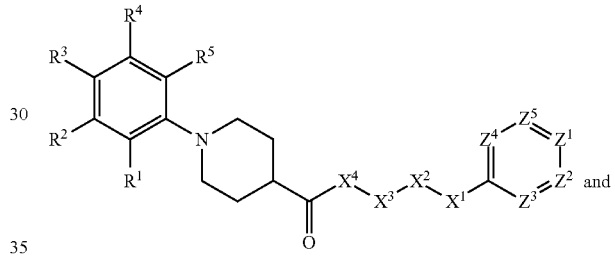

and

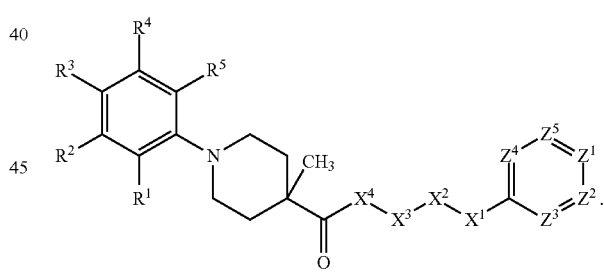

In some such embodiments, $X^4$ is —NH— optionally substituted with $C_1$-$C_6$-alkyl.

In some embodiments, the compound is selected from the group consisting of:

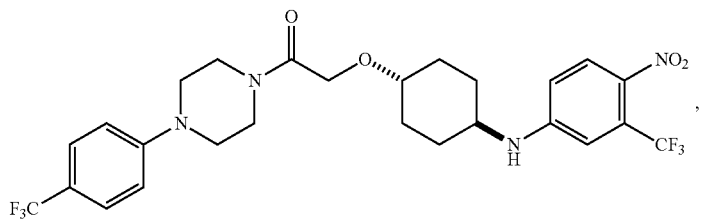

,

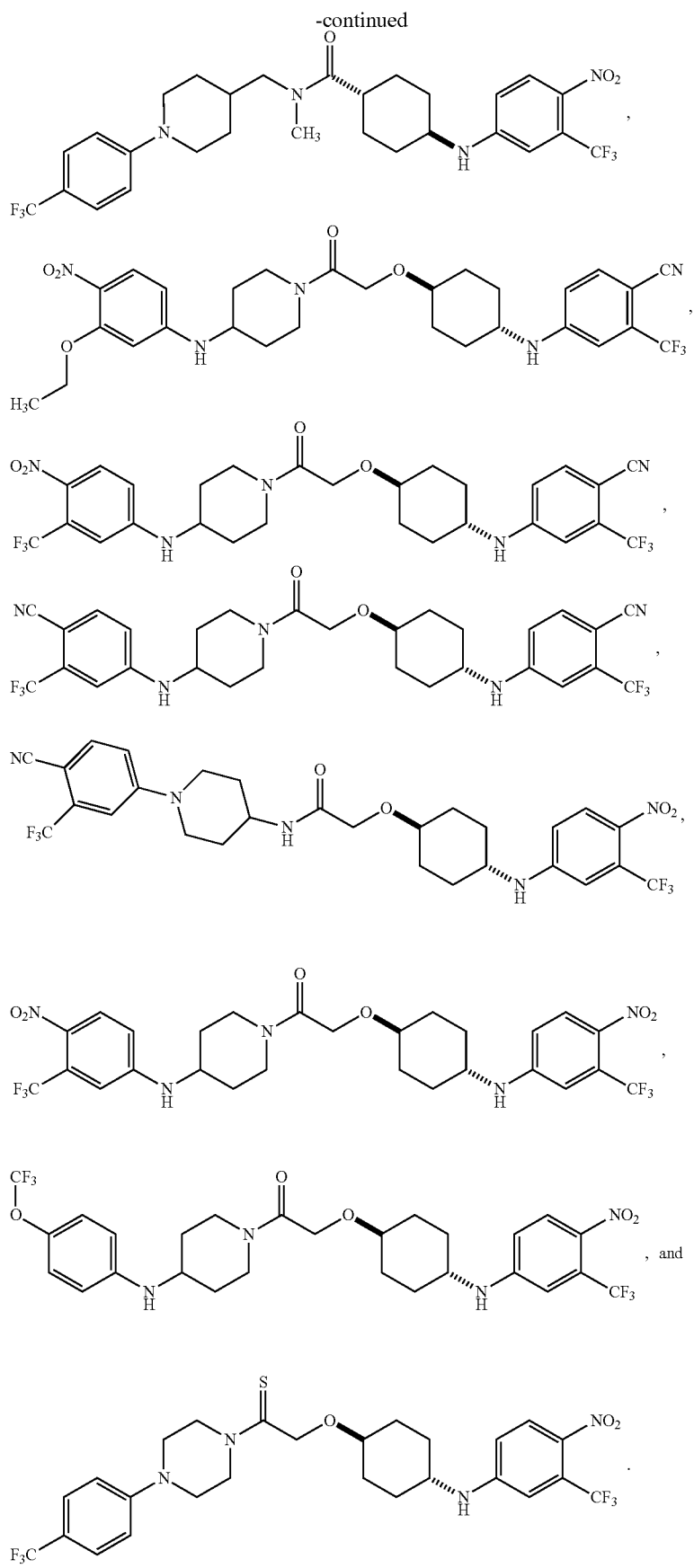

These compounds exhibited a lack undesirable toxicity levels in at least one toxicity study conducted by Applicants. In some embodiments, the compound is selected from the group consisting of:

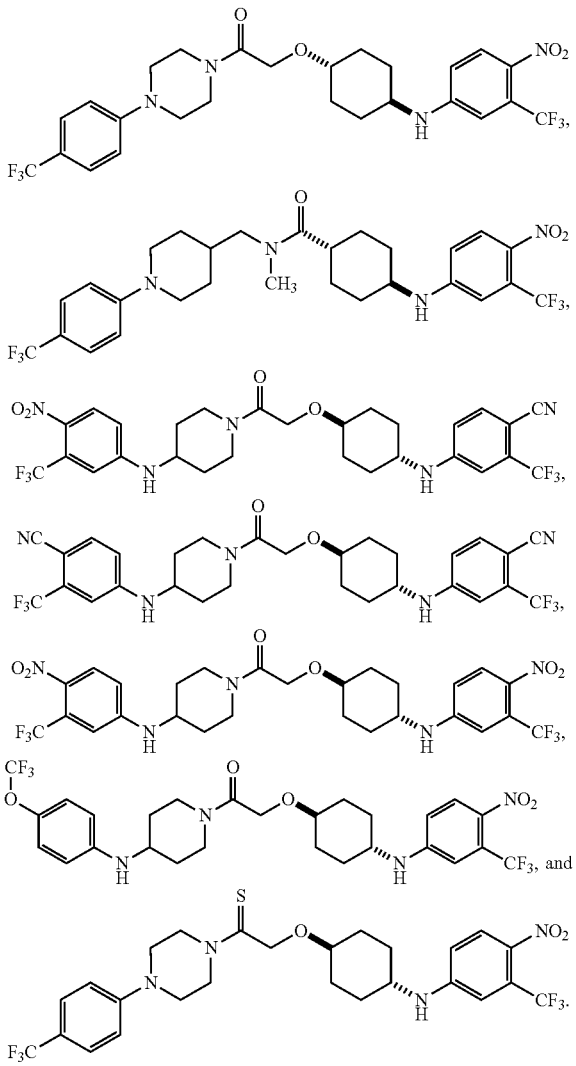

K. Isomers

In some embodiments, a compound of this invention may have two or more conformational structures. For example, the following compound can have a cis or trans configuration:

In some embodiments, this compound has the trans configuration such that the compound is encompassed by following formula:

In other embodiments, the compound has the cis configuration such that the compound is encompassed by the following formula:

Unless otherwise stated, a compound structure that does not indicate a particular conformation is intended to encompass compositions of all the possible conformational isomers of the compound, as well as compositions comprising fewer than all the possible conformational isomers.

In some embodiments, the compound of this invention is a chiral compound.

In some embodiments, the compound of this invention is a non-chiral compound.

II. Salts of Compounds for Use According to the Invention

A salt of the above-described compounds may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e., to an animal) for a therapeutic benefit, the salt preferably is pharmaceutically acceptable.

In general, an acid addition salt can be prepared by reacting a free base compound with an approximately stoichiometric amount of an inorganic or organic acid. Examples of often suitable inorganic acids for making pharmaceutically acceptable salts include hydrochloric, hydrobromic, hydroiodic, nitric, carbonic, sulfuric, and phosphoric acid. Examples of often suitable organic acids for making pharmaceutically acceptable salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

III. Treatment Methods Using Compounds and Salts of this Invention

In accordance with this invention, it has been discovered that the compounds and salts thereof are particularly useful for treating infections with *Dirofilaria immitis*. It is contemplated that the compounds and salts of this invention may be used to treat a range of animals, especially mammals, for example wild animals such as wolves, coyotes, foxes and raccoons and companion animals such as dogs, cats and ferrets.

The compounds and salts of this invention may be administered orally. For example, the compound or salt may be added to the intended recipient's feed, either directly or as part of a premix. The compound or salt alternatively may be administered as, for example, a separate solid dosage form (e.g., a tablet, a hard or soft capsule, granules, powders, etc.), paste, or liquid dosage form (e.g., a solution, suspension, syrup, etc.).

A dosage form may comprise one or more suitable excipients. Such excipients generally include, for example, sweetening agents, flavoring agents, coloring agents, preservative agents, inert diluents (e.g., calcium carbonate, sodium carbonate, lactose, calcium phosphate, sodium phosphate, or kaolin), granulating and disintegrating agents (e.g., corn starch or alginic acid), binding agents (e.g., gelatin, acacia, or carboxymethyl cellulose), and lubricating agents (e.g., magnesium stearate, stearic acid, or talc). The compounds may be premixed with the excipients or provided as separate entities, e.g. to be mixed at the site of administration (depending i.a. on the type of excipients, desired stability, transport requirements, desired ease of use etc.). A solid dispersion of particular use may be based on a polymer or graft copolymer, e.g. of polyethylene glycol, polyvinyl caprolactam, polyvinyl acetate and/or combinations thereof, amenable to solid dispersion techniques such as hot melt extrusion, spray drying and top spray granulation. The polymer may serve as a carrier for the active compound for use according to the invention. In particular a mixture of such a compound (about 5 g) and of a graft copolymer amenable to solid dispersion techniques such as a polyvinyl caprolactam-polyvinyl acetate-polyethylene glycol graft copolymer (about 10 g) is homogenized for about 20 minutes. Extrusion of the powder mixture is then performed using an extrusion equipment preheated at about 200° C. The obtained extrudate is then cooled down to room temperature; is ground to a fine powder for about 30 minutes using a ball mill. About 12 g of powdered extrudate is finally isolated.

Liquid compositions will generally comprise a solvent, such as, for example, one or more of dimethylformamide, N,N-dimethylacetamide, pyrrolidone, N-methylpyrrolidone, polyethyleneglycol, diethyleneglycolmonoethyl ester, dimethylsulfoxide, andethyl lactate. The solvent preferably has sufficient chemical properties and quantity to keep the compound or salt solubilized under normal storage conditions. In some instances, it may be desirable for the compositions to comprise one or more preservatives. The presence of a preservative may, for example, allow for the compositions to be stored for longer periods. Every excipient in the composition preferably is pharmaceutically acceptable.

It is contemplated that the compounds and salts of this invention may alternatively be administered via non-oral routes, such as rectally, via inhalation (e.g., via a mist or aerosol), transdermally (e.g., via a transdermal patch), or parenterally (e.g., subcutaneous injection, intravenous injection, intramuscular injection, etc.).

In general, the compositions of this invention are administered in a dosage form that provides a therapeutically effective amount of the compound or salt to the site of infection. A "therapeutically effective amount" is an amount that is sufficient to prevent, ameliorate, suppress, or eradicate a target pathogen(s) infection (which may be at any stage of the pathogen), which is equal to "treating an infection with the target pathogen". In particular for *Dirofilaria immitis*, by treating the infection, heartworm disease, i.e. any disorder arising from an infection with *Dirofilaria immitis*, is treated (i.e. prevented, ameliorated, suppressed or cured). Generally, the therapeutically effective amount is defined as the amount necessary to achieve a concentration efficacious to control the target pathogen(s) at the site of infection. The concentration at the site of infection is preferably at least equal to the $MIC_{100}$ level (minimum inhibitory concentration, i.e., the concentration that inhibits the motility of 100% of the target pathogen) of the compound or salt thereof for the target pathogen. To the extent the compound or salt is administered with another active ingredient(s) (e.g., one or more other anthelmintics), the dosage preferably comprises an amount of the compound or salt that, together with the amount of other active ingredient(s), constitutes a therapeutically effective amount.

A single administration of the compound or salt may be sufficient to treat an infection with *Dirofilaria immitis*. Although such a single dose is typically preferred, it is contemplated that multiple doses can be used. When the compound or salt is orally administered, the total dose to treat an infection is generally greater than about 0.01 mg/kg (i.e., milligram of compound or salt per kilogram body weight). In some such embodiments, the total dose is from about 0.01 to about 100 mg/kg, from about 0.01 to about 50 mg/kg, from about 0.1 to about 25 mg/kg, or from about 1 to about 20 mg/kg. For dogs, for example, the dose is generally from about 1 to about 15 mg/kg, from about 8 to about 12 mg/kg, or about 10 mg/kg. The same dose range may be suitable for other routes of administration. For example, in some embodiments, the same dose range is used for subcutaneous administration. The desired dose, however, may be less in some instances where the compound or salt is administered parenterally, particularly intravenously. For example, in some such embodiments, the dose is from about 0.01 to about 50 mg/kg, from about 0.01 to about 15 mg/kg, or from about 0.1 to about 10 mg/kg. For dogs, for example, a suitable intravenous dose may be from about 0.01 to about 10 mg/kg, from about 0.1 to about 5 mg/kg, or about 1 mg/kg.

If the compound or salt is administered parenterally via an injection, the concentration of the compound or salt in the dosage form preferably is sufficient to provide the desired therapeutically effective amount of the compound or salt in a volume that is acceptable for parenteral administration.

Factors affecting the preferred dosage may include, for example, the type (e.g., species and breed), age, size, sex, diet, activity, and condition of the intended recipient; the administration route; pharmacological considerations, such as the activity, efficacy, pharmacokinetic, and toxicology profiles of the particular composition administered; and whether the compound or salt is being administered as part of a combination of active ingredients. Thus, the preferred amount of the compound or salt can vary, and, therefore, can deviate from the typical dosages set forth above. Determining such dosage adjustments is generally within the skill of those in the art.

This invention is also directed to combinations which are useful for pharmaceutical compositions comprising a) one or more compounds for use according to the invention with b) one or more active compounds which differ in structure from component a). The active compounds b) are preferably anthelmintic compounds, more preferably selected from the group consisting of avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); benzimidazole derivatives, such as a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole, flubendazole, and triclabendazole); an imidazothiazoles (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzoenedisulphonamides (e.g., clorsulon); pyrazinaisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); amino-acetonitrile compounds (e.g. monepantel, AAD 1566); and amidine compounds (e.g., amidantel and tribendimidin) (including all pharmaceutically acceptable forms, such as salts).

In the contemplated combination therapies, the compounds for use according to this invention may be administered before, simultaneously, and/or after the other active ingredient(s). In addition, the compounds for use according to this invention may be administered in the same composition as the other active ingredient(s) and/or in a separate compositions from the other active ingredient(s). Further, the compounds for use according to this invention and other active ingredient(s) may be administered via the same and/or different routes of administration.

EXAMPLES

The following examples are merely illustrative, and not limiting to the remainder of this disclosure in any way.

Example 1. Protocols for Analyzing Compounds Prepared for Use in the Invention

Applicants prepared a plethora of compounds for use in the present invention. The identities and purities were characterized and verified using various analytical high performance liquid chromatography ("HPLC") and mass spectroscopy ("MS") protocols. These protocols are discussed below.

System I

In some instances, the compound analysis was conducted using an HPLC/MSD 1100 (Agilent, Santa Clara, Calif., USA) having a binary pump (G1312A) with a degasser (G1379A), a well plate sampler (G1367A), a column oven (G1316A), a diode array detector (G1315B), a mass detector (G1946D SL) with an ESI-source, and an evaporating light detector (Sedex 75). Four different columns and detection methods were used with this system:

Protocol I-A

The column used for this protocol was a Zorbax SB-C18 (Agilent), having a 4.6 mm diameter, a 30 mm length, and 3.5 μm packing. The column was operated at 30° C. (ambient temperature). The injection volume was 5.0 μL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
| --- | --- | --- |
| 0.0 | 90 | 10 |
| 0.2 | 90 | 10 |
| 4.2 | 2 | 98 |
| 5.5 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

Protocol I-B

The column used for this protocol was an Atlantis dC18 (Waters, Milford, Mass., USA), having a 4.6 mm diameter, a 50 mm length, and 3 μm packing. The column was operated at 30° C. The injection volume was 2.0 μL, the flow rate was 1.0 ml/min, and the run time was 10 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
| --- | --- | --- |
| 0.0 | 95 | 5 |
| 1.0 | 95 | 5 |
| 5.0 | 2 | 98 |
| 7.0 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

Protocol I-C

The column used for this protocol was an Atlantis dC18, having a 4.6 mm diameter, a 50 mm length, and 3 μm packing. The column was operated at 30° C. The injection volume was 2.0 μL, the flow rate was 1.5 ml/min, and the run time was 6 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
| --- | --- | --- |
| 0.0 | 90 | 10 |
| 0.5 | 90 | 10 |
| 3.0 | 2 | 98 |
| 4.0 | 2 | 98 |

The samples were diluted in a 1:1 mixture of solvents A and B before analysis. The detection methods were UV at 210 and 254 nm; ESI/MS (85-1000 m/z), positive ions; and ELSD (Sedex 75).

Protocol I-D

The column used for this protocol was a Zorbax SB-C18 (Agilent), having a 4.6 mm diameter, a 30 mm length, and 3.5 μm packing. The column was operated at 30° C. (ambient temperature). The injection volume was 5.0 μL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
| --- | --- | --- |
| 0.0 | 50 | 50 |
| 0.2 | 50 | 50 |
| 4.2 | 2 | 98 |
| 5.5 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

Protocol I-E

The column used for this protocol was a Chromolith Fast Gradient, RP-18e, 2 mm diameter and a 50 mm length. The column was operated at 35° C. The injection volume was 1.0 μL, the flow rate was 1.2 mL/min, and the run time was 3.5 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
| --- | --- | --- |
| 0.0 | 98 | 2 |
| 2.0 | 2 | 98 |
| 2.5 | 2 | 98 |
| 3.0 | 98 | 2 |

The samples were diluted in a 1:1 mixture of A and B before analysis. The detection methods were UV at 210 and 254 nm; ESI/MS (100-1000 m/z), positive ions; and ELSD (Sedex 75).

Protocol I-F

The column used for this protocol was a Chromolith Fast Gradient, RP-18e, 2 mm diameter and a 50 mm length. The column was operated at 35° C. The injection volume was 1.0 μL, the flow rate was 1.2 mL/min, and the run time was 3.5 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
| --- | --- | --- |
| 0.0 | 90 | 10 |
| 2.0 | 0 | 100 |
| 2.5 | 0 | 100 |
| 3.0 | 90 | 10 |

The samples were diluted in a 1:1 mixture of A and B before analysis. The detection methods were UV at 210 and 254 nm; ESI/MS (100-1000 m/z), positive ions; and ELSD (Sedex 75).

System II

In some instances, the compound analysis was conducted using an LC/MSD Trap 1100 (Agilent, Santa Clara, Calif., USA) having a binary pump (G1312A) with a degasser (G1379A), a well plate sampler (G1367A), a column oven (G1316A), a diode array detector (G1315B), a mass detector (G2445D SL) with an APCI-source, and an evaporating light detector (Alltech ELSD2000). Three different columns and detection methods were used with this system:

Protocol II-A

The column used for this protocol was a Zorbax SB-C18 (Agilent), having a 4.6 mm diameter, a 30 mm length, and 3.5 μm packing. The column was operated at 30° C. The injection volume was 5.0 μL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
| --- | --- | --- |
| 0.0 | 90 | 10 |
| 0.2 | 90 | 10 |
| 4.2 | 2 | 98 |
| 5.5 | 2 | 98 |

The samples were diluted in a 1:1 mixture of solvents A and B before analysis. The detection methods were UV at 210 and 254 nm; and APCI/MS (80-1000 m/z), positive ions.

Protocol II-B

The column used for this protocol was an XBridge C18 (Waters), having a 4.6 mm diameter, a 50 mm length, and 2.5 μm packing. The column was operated at 40° C. The injection volume was 2.0 μL, the flow rate was 1.0 ml/min, and the run time was 10 min (equilibration included). Two eluents were used with the following gradients:

| Time (min) | Solvent A (%) water/ammonia, 99.9/0.1 (v/v) | Solvent B (%) acetonitrile |
| --- | --- | --- |
| 0.0 | 75 | 25 |
| 5.0 | 0 | 100 |
| 7.0 | 0 | 100 |
| 7.5 | 75 | 25 |

The samples were diluted in a 1:1 mixture of solvents A and B before analysis. The detection methods were UV at 254 and 210 nm; and APCI/MS (100-1500 m/z), positive ions.

Protocol II-C

The column used for this protocol was a Gemini® C18 (Phenomenex Inc., CA) having a 4.6 mm diameter, a 50 mm length, and 5.0 μm packing. The column was operated at 35° C. The injection volume was 2.0 μL, and the flow rate was 1.0 ml/min. Two eluents were used with the following gradients:

| Time (min) | Solvent A (%) water/formic acid, 99.9/0.1 (v/v) | Solvent B (%) acetonitrile/formic acid, 99.9/0.1 (v/v) |
| --- | --- | --- |
| 0.0 | 98 | 2 |
| 3.5 | 2 | 98 |
| 6.0 | 2 | 98 |

The samples were diluted in a 1:1 mixture of solvents A and B before analysis. The detection methods were UV at 270 nm; and APCI/MS (100-800 m/z), positive and negative ions.

Exemplified Compounds

Compounds or salts thereof for use in the present invention are generally described in WO2009/077527. The examples 2 to 57 of WO2009/077527 (pages 57-108) are incorporated in this application as examples of compounds for use in the present invention, as well as methods of preparation thereof. The same is true for examples 58 through 265 which are exemplified in table II of WO2009/077527 (page 108-137).

Additional examples of compounds for use in the present invention are described here beneath. A first new compound (Example 266) is made as follows:

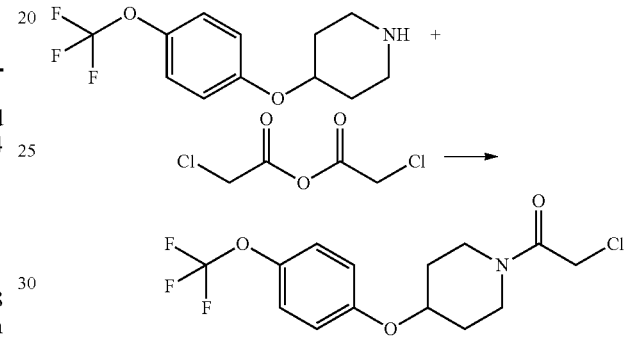

4-[4-(trifluoromethoxy)phenoxy]piperidine (2 g; 7.7 mmol) is suspended in dichloromethane (25 mL) and a solution of chloroacetic acid anhydride (1.35 g; 7.7 mmol) in dichloromethane (5 mL) is slowly added under stirring. After 140 min reaction time, extra chloroacetic acid anhydride (575 mg; 3.3 mmol) is added and the reaction mixture is stirred overnight. The reaction mixture is washed with aq. 0.2 M hydrochloric acid (2×30 mL) and aq. 1 M sodium hydroxide (50 mL). The organic phase is dried over sodium sulfate, filtered and concentrated under reduced pressure to afford the desired product (2.1 g; 6.2 mmol) as a crude which is engaged in the next step as such.

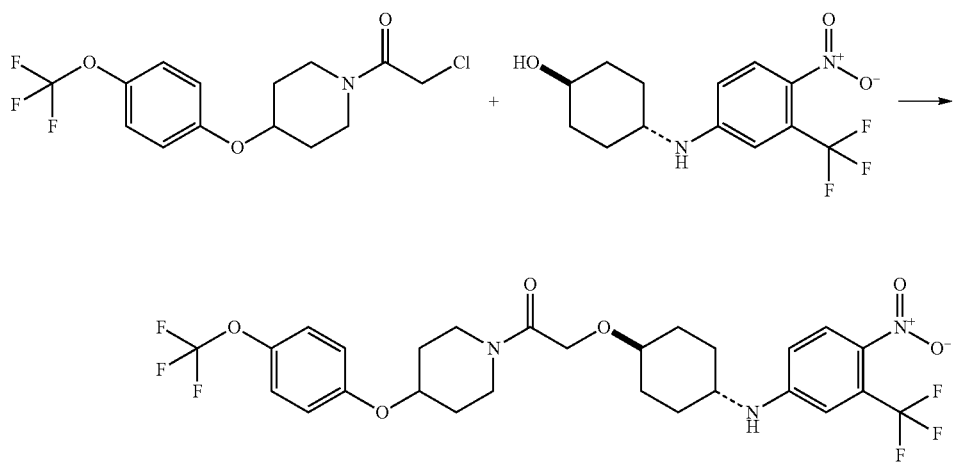

2-chloro-1-[4-[4-(trifluoromethoxy)phenoxy]-1-piperidyl]ethanone (23 g; 68 mmol) and 4-[4-nitro-3-(trifluoromethyl)anilino]cyclohexanol (20.7 g; 68 mmol) are dissolved in a mixture of tetrahydrofuran (6 mL) and dichloromethane (300 mL). Sodium iodide (10.3 g; 68 mmol) and sodium hydroxide (9.8 g; 238 mmol) are added and the resulting mixture is stirred at reflux for 6.5 h. After cooling to room temperature, water (300 mL) is added and the two phases are stirred for 10 min. The organic phase is separated and is washed with 1 M hydrochloric acid (200 mL), aq. sat. sodium chloride (2×250 mL), dried over sodium sulfate and concentrated under reduced pressure to afford the desired product as a crude. Recrystallization from ethanol yield the desired product in pure form. The structure was confirmed using Protocol I-F. Calculated mass=605; observed mass=605; HPLC retention time=2.16 min (compound 266).

A next compound (Example 267) is made as follows:

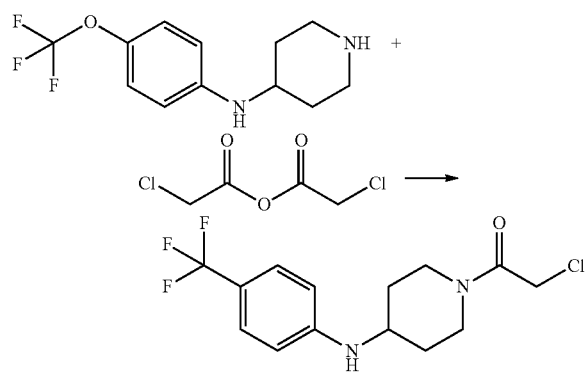

N-[4-(trifluoromethyl)phenyl]piperidin-4-amine (2 g; 8.2 mmol) is suspended in dichloromethane (25 mL) and a solution of chloroacetic acid anhydride (1.44 g; 8.2 mmol) in dichloromethane (5 mL) is slowly added under stirring. After 90 min reaction time, the reaction mixture is washed with aq. 0.2 M hydrochloric acid (2×30 mL) and aq. 1 M sodium hydroxide (50 mL). The organic phase is dried over sodium sulfate, filtered and concentrated under reduced pressure to afford the desired product (2.5 g; 7.8 mmol) as a crude which is engaged in the next step as such.

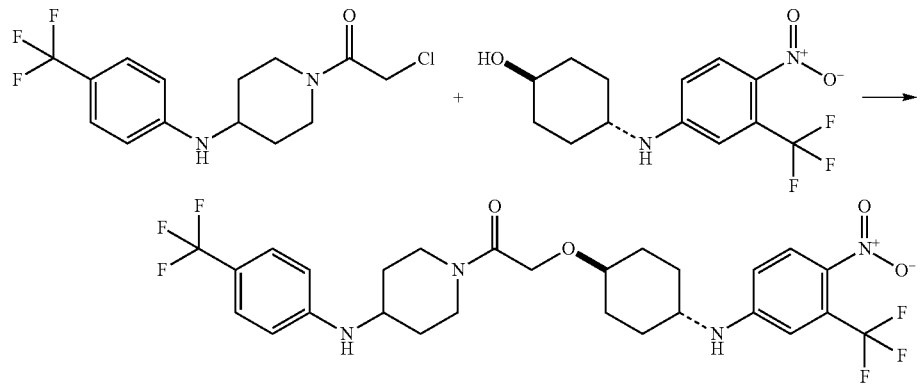

2-chloro-1-[4-[4-(trifluoromethyl)anilino]-1-piperidyl]ethanone (24.2 g; 75 mmol) and 4-[4-nitro-3-(trifluoromethyl)anilino]cyclohexanol (23 g; 75 mmol) are dissolved in a mixture of tetrahydrofuran (5 mL) and dichloromethane (250 mL). Sodium iodide (11.4 g; 75 mmol) and sodium hydroxide (10.9 g; 264 mmol) are added and the resulting mixture is stirred at reflux for 5 h. After cooling to room temperature, water (250 mL) is added and the two phases are stirred for 5 min. The organic phase is separated and the aqueous phase is extracted twice with dichloromethane (250 mL each). The combined organic layers are washed with aq. sat. sodium chloride (500 mL), dried over sodium sulfate and concentrated under reduced pressure to afford the desired product as a crude. Recrystallization from ethanol yield the desired product in pure form (18.5 g; 31 mmol). The structure was confirmed using Protocol I-E. Calculated mass=588; observed mass=588; HPLC retention time=2.24 min (compound 267).

Example 268. Determining Activity Against *Dirofilaria immitis*

Microfilariae recovered from *D. immitis* infected dogs were plated in 96-well plates under sterile conditions. L3 larvae of *D. immitis* were recovered from infected mosquitoes and allowed to molt into L4 stages required for compound testing. L4 larvae were plated in 96-well plates under sterile conditions. DMSO solutions of the compounds were added into parasite-containing plates. After compound addition, parasites were incubated for 3 days prior to assessment of viability. Microfilaricidal activity is reported as a half maximal effective concentration ($EC_{50}$). Effects on L4 larvae are reported as the lowest doses that result in complete loss of motility ($MIC_{100}$).

Compounds according to Examples 267, 263 (see WO2009/077527), 247 (see WO2009/077527), 195 (see WO2009/077527), 194 (see WO2009/077527), 183 (see WO2009/077527), 180 (see WO2009/077527), 160 (see WO2009/077527), 57 (see WO2009/077527), 13 (see WO2009/077527) and 12 (see WO2009/077527) exhibited $EC_{50}$ values of less than 10 µM against *D. immitis* microfilariae. Compounds according to example 266, 249 (see WO2009/077527), 196 (see WO2009/077527), 189 (see WO2009/077527), 178 (see WO2009/077527), 174 (see WO2009/077527), 172 (see WO2009/077527), 170 (see WO2009/077527), 11 (see WO2009/077527) and 10 (see WO2009/077527) exhibited $EC_{50}$ values of less than 5 µM against *D. immitis* microfilariae.

Compounds according to examples 266, 267, 194 (see WO2009/077527), 57 (see WO2009/077527) and 11 (see WO2009/077527) exhibited $MIC_{100}$ values of less than 10 µM against L4 larvae of *D. immitis*. Compounds according to examples 263 (see WO2009/077527), 247 (see WO2009/077527), 195 (see WO2009/077527), 189 (see WO2009/077527), 183 (see WO2009/077527), 180 (see WO2009/077527), 178 (see WO2009/077527), 174 (see WO2009/077527), 160 (see WO2009/077527), 13 (see WO2009/077527) and 12 (see WO2009/077527) exhibited MIC$_{100}$ values of less than 5 μM against L4 larvae of *D. immitis*.

Definitions

The term "alkyl" (alone or in combination with another term(s)) means a straight- or branched-chain saturated hydrocarbyl substituent (i.e., a substituent containing only carbon and hydrogen) typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, iso-butyl, sec-butyl, tert-butyl, pentyl, iso-amyl, hexyl, and octyl.

The term "alkenyl" (alone or in combination with another term(s)) means a straight- or branched-chain hydrocarbyl substituent containing one or more double bonds and typically from 2 to about 20 carbon atoms, more typically from about 2 to about 20 carbon atoms, even more typically from about 2 to about 8 carbon atoms, and still even more typically from about 2 to about 6 carbon atoms. Examples of such substituents include ethenyl (vinyl); 2-propenyl; 3-propenyl; 1,4-pentadienyl; 1,4-butadienyl; 1-butenyl; 2-butenyl; 3-butenyl; and decenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, decynyl, 1-butynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent typically containing from 3 to 14 carbon ring atoms ("ring atoms" are the atoms bound together to form the ring or rings of a cyclic moiety). A carbocyclyl may be a single ring, which typically contains from 3 to 6 ring atoms. Examples of such single-ring carbocyclyls include cyclopropanyl, cyclobutanyl, cyclopentyl, cyclopentenyl, cyclopentadienyl, cyclohexyl, cyclohexenyl, cyclohexadienyl, and phenyl. A carbocyclyl alternatively may be multiple (typically 2 or 3) rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluorenyl, decalinyl, and norpinanyl.

The term "cycloalkyl" (alone or in combination with another term(s)) means a saturated cyclic hydrocarbyl substituent typically containing from 3 to 14 carbon ring atoms. A cycloalkyl may be a single carbon ring, which typically contains from 3 to 6 carbon ring atoms. Examples of single-ring cycloalkyls include cyclopropyl (or "cyclopropanyl"), cyclobutyl (or "cyclobutanyl"), cyclopentyl (or "cyclopentanyl"), and cyclohexyl (or "cyclohexanyl"). A cycloalkyl alternatively may be multiple (typically 2 or 3) carbon rings fused together, such as, decalinyl or norpinanyl.

The term "aryl" (alone or in combination with another term(s)) means an aromatic carbocyclyl typically containing from 6 to 14 carbon ring atoms. Examples of aryls include phenyl, naphthalenyl, and indenyl.

In some instances, the number of carbon atoms in a hydrocarbyl group (e.g., alkyl, alkenyl, alkynyl, or cycloalkyl) is indicated by the prefix "$C_x$-$C_y$-", wherein x is the minimum and y is the maximum number of carbon atoms in the group. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical (or "hydrido"), and may be depicted as —H.

The term "hydroxy" (alone or in combination with another term(s)) means —OH.

The term "nitro" (alone or in combination with another term(s)) means —NO$_2$.

The term "cyano" (alone or in combination with another term(s)) means —CN, which also may be depicted:

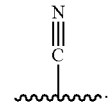

The term "oxo" (alone or in combination with another term(s)) means an oxo radical, and may be depicted as:

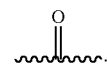

The term "carboxy" (alone or in combination with another term(s)) means —C(O)—OH, which also may be depicted as:

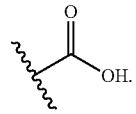

The term "amino" (alone or in combination with another term(s)) means —NH$_2$.

The term "halogen" (alone or in combination with another term(s)) means a fluorine radical ("fluoro", which may be depicted as —F), chlorine radical ("chloro", which may be depicted as —Cl), bromine radical ("bromo", which may be depicted as —Br), or iodine radical ("iodo", which may be depicted as —I). Typically, fluoro or chloro is preferred, with fluoro often being particularly preferred.

If a substituent is described as being "substituted", a non-hydrogen substituent is in the place of a hydrogen on a carbon, nitrogen, oxygen, or sulfur of the substituent. Thus, for example, a substituted alkyl substituent is an alkyl substituent wherein at least one non-hydrogen substituent is in the place of a hydrogen on the alkyl substituent. To illustrate, monofluoroalkyl is alkyl substituted with a fluoro, and difluoroalkyl is alkyl substituted with two fluoros. It should be recognized that if there are more than one substitutions on a substituent, each non-hydrogen substituent may be identical or different (unless otherwise stated).

If a substituent is described as being "optionally substituted", the substituent may be either (1) not substituted or (2)

substituted. If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 substituents, then any heteroaryl with less than 3 substitutable positions would be optionally substituted by up to only as many non-hydrogen substituents as the heteroaryl has substitutable positions. To illustrate, tetrazolyl (which has only one substitutable position when it is bonded to a single non-hydrogen moiety by a single bond) would be optionally substituted with up to one non-hydrogen substituent. To illustrate further, if an amino nitrogen is described as being optionally substituted with up to 2 non-hydrogen substituents, then a primary amino nitrogen will be optionally substituted with up to 2 non-hydrogen substituents, whereas a secondary amino nitrogen will be optionally substituted with up to only one non-hydrogen substituent.

The prefix "halo" indicates that the substituent to which the prefix is attached is substituted with one or more independently selected halogens. For example, haloalkyl means an alkyl substituent having a halogen in the place of a hydrogen, or multiple halogens in the place of the same number of hydrogens. Examples of haloalkyls include chloromethyl, 1-bromoethyl, fluoromethyl, difluoromethyl, trifluoromethyl, and 1,1,1-trifluoroethyl. Illustrating further, "haloalkoxy" means an alkoxy substituent wherein a halogen is in the place of a hydrogen, or multiple halogens are in the place of the same number of hydrogens. Examples of haloalkoxy substituents include chloromethoxy, 1-bromoethoxy, fluoromethoxy, difluoromethoxy, trifluoromethoxy (also known as "perfluoromethyloxy"), and 1,1,1,-trifluoroethoxy. It should be recognized that if a substituent is substituted by more than one halogen, the halogens may be identical or different (unless otherwise stated).

The term "carbonyl" (alone or in combination with another term(s)) means —C(O)—, which also may be depicted as:

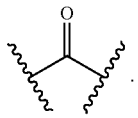 [SMILES: *C(*)=O]

This term also is intended to encompass a hydrated carbonyl substituent, i.e., —C(OH)₂—.

The term "aminocarbonyl" (alone or in combination with another term(s)) means —C(O)—NH₂, which also may be depicted as:

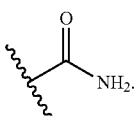

The term "oxy" (alone or in combination with another term(s)) means an ether substituent, and may be depicted as —O—.

The term "alkoxy" (alone or in combination with another term(s)) means an alkylether substituent, i.e., —O-alkyl. Examples of such a substituent include methoxy (—O—CH₃), ethoxy, n-propoxy, iso-propoxy, n-butoxy, iso-butoxy, sec-butoxy, and tert-butoxy.

The term "alkylcarbonyl" (alone or in combination with another term(s)) means —C(O)-alkyl. For example, "ethylcarbonyl" may be depicted as:

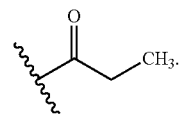 [SMILES: *C(=O)CC]

The term "alkoxycarbonyl" (alone or in combination with another term(s)) means —C(O)—O-alkyl. For example, "ethoxycarbonyl" may be depicted as:

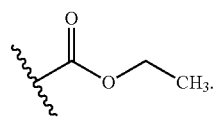 [SMILES: *C(=O)OCC]

The term "carbocyclylcarbonyl" (alone or in combination with another term(s)) means —C(O)-carbocyclyl. For example, "phenylcarbonyl" may be depicted as:

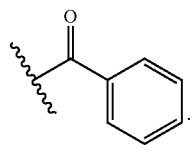 [SMILES: *C(=O)c1ccccc1]

Similarly, the term "heterocyclylcarbonyl" (alone or in combination with another term(s)) means —C(O)-heterocyclyl.

The term "sulfanyl" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-sulfanyl-alkyl" means alkyl-S-alkyl.

The term "thiol" or "mercapto" (alone or in combination with another term(s)) means a sulfhydryl substituent, and may be depicted as —SH.

The term "thiocarbonyl" (alone or in combination with another term(s)) means a carbonyl wherein a sulfur is in the place of the oxygen. Such a substituent may be depicted as —C(S)—, and also may be depicted as:

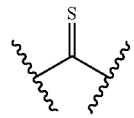

The term "sulfonyl" (alone or in combination with another term(s)) means —S(O)₂—, which also may be depicted as:

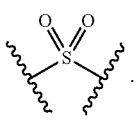 [SMILES: *S(*)(=O)=O]

Thus, for example, "alkyl-sulfonyl-alkyl" means alkyl-S(O)$_2$-alkyl.

The term "aminosulfonyl" (alone or in combination with another term(s)) means —S(O)$_2$—NH$_2$, which also may be depicted as:

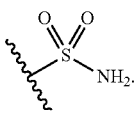

The term "sulfinyl" (alone or in combination with another term(s)) means —S(O)—, which also may be depicted as:

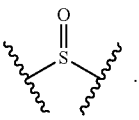

Thus, for example, "alkyl-sulfinyl-alkyl" means alkyl-S(O)-alkyl.

The term "heterocyclyl" (alone or in combination with another term(s)) means a saturated (i.e., "heterocycloalkyl"), non-aromatic partially-saturated (i.e., "heterocycloalkenyl"), or heterocyclic aromatic (i.e., "heteroaryl") ring structure typically containing a total of 3 to 14 ring atoms. At least one of the ring atoms is a heteroatom (typically oxygen, nitrogen, or sulfur), with the remaining ring atoms generally being independently selected from the group typically consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, thienyl (also known as "thiophenyl" and "thiofuranyl"), oxazolyl, isoxazolyl, thiazolyl, isothiazolyl, thiodiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), pyrrolyl, pyrazolyl, imidazolyl, triazolyl, tetrazolyl, oxathiazolyl, oxatriazolyl (including 1,2,3,4-oxatriazolyl and 1,2,3,5-oxatriazolyl), pyridinyl, diazinyl (including pyridazinyl (also known as "1,2-diazinyl"), pyrimidinyl (also known as "1,3-diazinyl"), and pyrazinyl (also known as "1,4-diazinyl")), triazinyl (including s-triazinyl (also known as "1,3,5-triazinyl"), as-triazinyl (also known 1,2,4-triazinyl), and v-triazinyl (also known as "1,2,3-triazinyl")), oxathiazinyl (including 1,2,5-oxathiazinyl and 1,2,6-oxathiazinyl), oxepinyl, thiepinyl, dihydrofuranyl, tetrahydrofuranyl, dihydrothienyl (also known as "dihydrothiophenyl"), tetrahydrothienyl (also known as "tetrahydrothiophenyl"), isopyrrolyl, pyrrolinyl, pyrrolidinyl, isoimidazolyl, imidazolinyl, imidazolidinyl, pyrazolinyl, pyrazolidinyl, dithiolyl, oxathiolyl, oxathiolanyl, oxazolidinyl, isoxazolidinyl, thiazolinyl, isothiazolinyl, thiazolidinyl, isothiazolidinyl, dioxazolyl (including 1,2,3-dioxazolyl, 1,2,4-dioxazolyl, 1,3,2-dioxazolyl, and 1,3,4-dioxazolyl), pyranyl (including 1,2-pyranyl and 1,4-pyranyl), dihydropyranyl, tetrahydropyranyl, piperidinyl, piperazinyl, oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxadiazinyl (including 1,4,2-oxadiazinyl and 1,3,5,2-oxadiazinyl), morpholinyl, azepinyl, and diazepinyl.

A heterocyclyl alternatively may be 2 or 3 rings fused together, such as, for example, indolizinyl, pyranopyrrolyl, purinyl, imidazopyrazinyl, imidazolopyridazyl, pyridopyridinyl (including pyrido[3,4-b]-pyridinyl, pyrido[3,2-b]-pyridinyl, pyrido[4,3-b]-pyridinyl, and naphthyridinyl), pteridinyl, pyridazinotetrazinyl, pyrazinotetrazinyl, pyrimidinotetrazinyl, pyrindinyl, pyrazolopyrimidinyl, pyrazolopyrazinyl, pyrazolopyridazyl, or 4H-quinolizinyl. In some embodiments, the preferred multi-ring heterocyclyls are indolizinyl, pyranopyrrolyl, purinyl, pyridopyridinyl, pyrindinyl, and 4H-quinolizinyl.

Other examples of fused-ring heterocyclyls include benzo-fused heterocyclyls, such as, for example, benzofuranyl (also known as "coumaronyl"), isobenzofuranyl, benzoxazolyl, benzoisoxazolyl (also known as "indoxazinyl"), anthranilyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzoisothiazolyl, benzothiadiazolyl, benzoxadiazolyl, indolyl, isoindazolyl (also known as "benzpyrazolyl"), benzoimidazolyl, benzotriazolyl, benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzoimidazothiazolyl, carbazolyl, acridinyl, isoindolyl, indoleninyl (also known as "pseudoindolyl"), benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, benzoxazinyl (including 1,3,2-benzoxazinyl, 1,4,2-benzoxazinyl, 2,3,1-benzoxazinyl, and 3,1,4-benzoxazinyl), benzoisoxazinyl (including 1,2-benzisoxazinyl and 1,4-benzisoxazinyl), benzoxadiazinyl, and xanthenyl. In some embodiments, the preferred benzo-fused heterocyclyls are benzofuranyl, isobenzofuranyl, benzoxazolyl, benzoisoxazolyl, anthranilyl, benzothienyl, isobenzothienyl, benzothiazolyl, benzothiadiazolyl, benzoxadiazolyl, indolyl, isoindazolyl, benzoimidazolyl, benzotriazolyl, benzazinyl, phthalazinyl, quinoxalinyl, benzodiazinyl, carbazolyl, acridinyl, isoindolyl, indoleninyl, benzodioxolyl, chromanyl, isochromanyl, thiochromanyl, benzodioxanyl, tetrahydroisoquinolinyl, benzoxazinyl, benzoisoxazinyl, and xanthenyl.

The term "2-fused-ring" heterocyclyl (alone or in combination with another term(s)) means a saturated, non-aromatic partially-saturated, or heteroaryl containing two fused rings. Such heterocyclyls include, for example, benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, imidazolopyridazyl, quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, pyrindinyl, isoindolyl, indoleninyl, pyrazolopyrimidinyl, pyrazolopyrazinyl, pyrazolopyridazyl, benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, 4H-quinolizinyl, benzoxazinyl, and benzoisoxazinyl. In some embodiments, preferred 2-fused-ring heterocyclyls include benzofuranyl, isobenzofuranyl, benzoxazolyl, benzoisoxazolyl, anthranilyl, benzothienyl, isobenzothienyl, benzothiazolyl, benzothiadiazolyl, indolizinyl, pyranopyrrolyl, benzoxadiazolyl, indolyl, isoindazolyl, benzoimidazolyl, benzotriazolyl, purinyl, quinolinyl, isoquinolinyl, pyridopyridinyl, phthalazinyl, quinoxalinyl, benzodiazinyl, pteridinyl, pyrindinyl, isoindolyl, indoleninyl, benzodioxolyl, benzodioxanyl, tetrahydroisoquinolinyl, 4H-quinolizinyl, benzoxazinyl, and benzoisoxazinyl.

The term "heteroaryl" (alone or in combination with another term(s)) means an aromatic heterocyclyl typically containing from 5 to 14 ring atoms. A heteroaryl may be a single ring or multiple (typically 2 or 3) fused rings. Such moieties include, for example, 5-membered rings such as furanyl, thienyl, oxazolyl, isoxazolyl, thiazolyl, isothiazolyl, thiodiazolyl, oxadiazolyl, pyrrolyl, pyrazolyl, imidazolyl, triazolyl, tetrazolyl, oxathiazolyl, and oxatriazolyl; 6-membered rings such as pyridinyl, pyrazinyl, pyrimidinyl, pyridazinyl, triazinyl, and oxathiazinyl; 7-membered rings such as oxepinyl and thiepinyl; 6/5-membered fused-ring systems such as benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, and imidazolopyridazyl; and 6/6-membered fused-ring systems such as quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, benzoimidazothiazinyl, carbazolyl, and acridinyl. In some embodiments, the preferred 5-membered rings include furanyl, thienyl, oxazolyl, isoxazolyl, thiazolyl, isothiazolyl, oxadiazolyl, pyrazolyl, and imidazolyl; the preferred 6-membered rings include pyridinyl, pyrazinyl, pyrimidinyl, pyridazinyl, and triazinyl; the preferred 6/5-membered fused-ring systems include benzoxazolyl, benzoisoxazolyl, anthranilyl, benzothienyl, isobenzothienyl, and purinyl; and the preferred 6/6-membered fused-ring systems include quinolinyl, isoquinolinyl, and benzodiazinyl.

A carbocyclyl or heterocyclyl can optionally be substituted with, for example, one or more substituents independently selected from the group consisting of halogen, hydroxy, carboxy, oxo, alkyl, alkoxy, alkoxyalkyl, alkylcarbonyl, aryl, arylalkyl, arylalkoxy, arylalkoxyalkyl, arylalkoxycarbonyl, cycloalkyl, cycloalkylalkyl, cycloalkylalkoxy, cycloalkylalkoxyalkyl, and cycloalkylalkoxycarbonyl. More typically, a carbocyclyl or heterocyclyl may optionally be substituted with, for example, one or more substituents independently selected from the group consisting of halogen, —OH, —C(O)—OH, oxo, $C_1$-$C_6$-alkyl, $C_1$-$C_6$-alkoxy, $C_1$-$C_6$-alkoxy-$C_1$-$C_6$-alkyl, $C_1$-$C_6$-alkylcarbonyl, aryl, aryl-$C_1$-$C_6$-alkyl, aryl-$C_1$-$C_6$-alkoxy, aryl-$C_1$-$C_6$-alkoxy-$C_1$-$C_6$-alkyl, aryl-$C_1$-$C_6$-alkoxycarbonyl, cycloalkyl, cycloalkyl-$C_1$-$C_6$-alkyl, cycloalkyl-$C_1$-$C_6$-alkoxy, cycloalkyl-$C_1$-$C_6$-alkoxy-$C_1$-$C_6$-alkyl, and cycloalkyl-$C_1$-$C_6$-alkoxycarbonyl. The alkyl, alkoxy, alkoxyalkyl, alkylcarbonyl, aryl, arylalkyl, arylalkoxy, arylalkoxyalkyl, or arylalkoxycarbonyl substituent(s) may further be substituted with, for example, one or more halogen. The aryl and cycloalkyl portions of such optional substituents are typically single-rings containing from 3 to 6 ring atoms, and more typically from 5 to 6 ring atoms.

An aryl or heteroaryl can optionally be substituted with, for example, one or more substituents independently selected from the group consisting of halogen, —OH, —CN, —NO$_2$, —SH, —C(O)—OH, amino, aminoalkyl, alkyl, alkylsulfanyl, carboxyalkylsulfanyl, alkylcarbonyloxy, alkoxy, alkoxyalkyl, alkoxycarbonylalkoxy, alkoxyalkylsulfanyl, alkoxycarbonylalkylsulfanyl, carboxyalkoxy, alkoxycarbonylalkoxy, carbocyclyl, carbocyclylalkyl, carbocyclyloxy, carbocyclylsulfanyl, carbocyclylalkylsulfanyl, carbocyclylamino, carbocyclylalkylamino, carbocyclylcarbonylamino, carbocyclylalkyl, carbocyclylcarbonyloxy, carbocyclyloxyalkoxycarbocyclyl, carbocyclylsulfanylalkylsulfanylcarbocyclyl, carbocyclylsulfanylalkoxycarbocyclyl, carbocyclyloxyalkylsulfanylcarbocyclyl, heterocyclyl, heterocyclylalkyl, heterocyclyloxy, heterocyclylsulfanyl, heterocyclylalkylsulfanyl, heterocyclylamino, heterocyclylalkylamino, heterocyclylcarbonylamino, heterocyclylcarbonyloxy, heterocyclyloxyalkoxyheterocyclyl, heterocyclylsulfanylalkylsulfanylheterocyclyl, heterocyclylsulfanylalkoxyheterocyclyl, and heterocyclyloxyalkylsulfanylheterocyclyl. More typically, an aryl or heteroaryl may, for example, optionally be substituted with one or more substituents independently selected from the group consisting of halogen, —OH, —CN, —NO$_2$, —SH, —C(O)—OH, amino, amino-$C_1$-$C_6$-alkyl, $C_1$-$C_6$-alkyl, $C_1$-$C_6$-alkylsulfanyl, carboxy-$C_1$-$C_6$-alkylsulfanyl, $C_1$-$C_6$-alkylcarbonyloxy, $C_1$-$C_6$-alkoxy, $C_1$-$C_6$-alkoxy-$C_1$-$C_6$-alkyl, $C_1$-$C_6$-alkoxycarbonyl-$C_1$-$C_6$-alkoxy, $C_1$-$C_6$-alkoxy-$C_1$-$C_6$-alkylsulfanyl, $C_1$-$C_6$-alkoxycarbonyl-$C_1$-$C_6$-alkylsulfanyl, carboxy-$C_1$-$C_6$-alkoxy, $C_1$-$C_6$-alkoxycarbonyl-$C_1$-$C_6$-alkoxy, aryl, aryl-$C_1$-$C_6$-alkyl, aryloxy, arylsulfanyl, aryl-$C_1$-$C_6$-alkylsulfanyl, arylamino, aryl-$C_1$-$C_6$-alkylamino, arylcarbonylamino, arylcarbonyloxy, aryloxy-$C_1$-$C_6$-alkoxyaryl, arylsulfanyl-$C_1$-$C_6$-alkylsulfanylaryl, arylsulfanyl-$C_1$-$C_6$-alkoxyaryl, aryloxy-$C_1$-$C_6$-alkylsulfanylaryl, cycloalkyl, cycloalkyl-$C_1$-$C_6$-alkyl, cycloalkyloxy, cycloalkylsulfanyl, cycloalkyl-$C_1$-$C_6$-alkylsulfanyl, cycloalkylamino, cycloalkyl-$C_1$-$C_6$-alkylamino, cycloalkylcarbonylamino, cycloalkylcarbonyloxy, heteroaryl, heteroaryl-$C_1$-$C_6$-alkyl, heteroaryloxy, heteroarylsulfanyl, heteroaryl-$C_1$-$C_6$-alkylsulfanyl, heteroarylamino, heteroaryl-$C_1$-$C_6$-alkylamino, heteroarylcarbonylamino, and heteroarylcarbonyloxy. Here, one or more hydrogens bound to a carbon in any such substituent may, for example, optionally be replaced with halogen. In addition, any cycloalkyl, aryl, and heteroaryl portions of such optional substituents are typically single-rings containing 3 to 6 ring atoms, and more typically 5 or 6 ring atoms.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component.

If substituents are described as being "independently selected," each substituent is selected independent of the other. Each substituent, therefore, may be identical to or different from the other selected substituent(s).

When words are used to describe a substituent, the rightmost-described component of the substituent is the component that has the free valence. To illustrate, benzene substituted with methoxyethyl has the following structure:

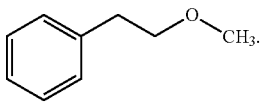

As can be seen, the ethyl is bound to the benzene, and the methoxy is the component of the substituent that is the component furthest from the benzene. As further illustration, benzene substituted with cyclohexanylsulfanylbutoxy has the following structure:

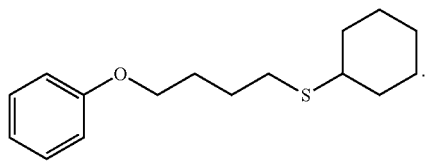 [SMILES: c1ccc(OCCCCSC2CCCCC2)cc1]

When a chemical formula is used to describe a monovalent substituent, the dash on the left side of the formula indicates the portion of the substituent that has the free valence. To illustrate, benzene substituted with —C(O)—OH has the following structure:

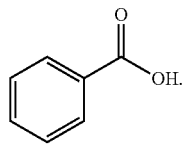

When a chemical formula is used to describe a di-valent (or "linking") component between two other components of a depicted chemical structure (the right and left components), the leftmost dash of the linking component indicates the portion of the linking component that is bound to the left component in the depicted structure. The rightmost dash, on the other hand, indicates the portion of the linking component that is bound to the right component in the depicted structure. To illustrate, if the depicted chemical structure is X-L-Y and L is described as —C(O)—N(H)—, then the chemical would be:

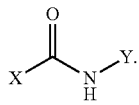

Dashes are not used to characterize a tri-valent component when standing alone. Thus, for example, a tri-valent nitrogen is identified as "N" and a tri-valent carbon bonded to hydrogen is identified as "CH" in this patent.

The words "comprise", "comprises", and "comprising" are to be interpreted inclusively rather than exclusively. This interpretation is intended to be the same as the interpretation that these words are given under United States patent law.

The term "pharmaceutically acceptable" is used adjectivally to mean that the modified noun is appropriate for use in a pharmaceutical product. When it is used, for example, to describe a salt or excipient, it characterizes the salt or excipient as being compatible with the other ingredients of the composition, and not deleterious to the intended recipient animal to the extent that the deleterious effect(s) outweighs the benefit(s) of the salt.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A method of treating an infection with *Dirofilaria immitis* comprising administering to a subject animal a compound or salt thereof, wherein the compound is selected from the group consisting of:

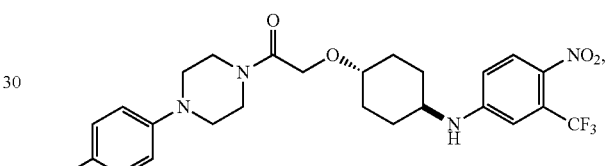

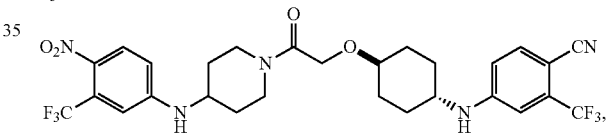

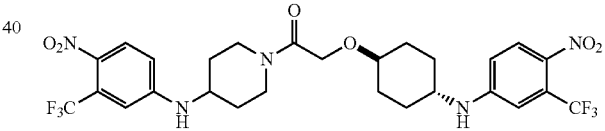

and

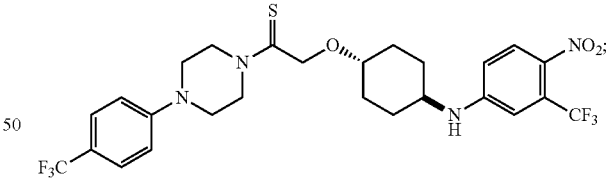

wherein the compound or salt is active against larval worms and microfilariae of *Dirofilaria immitis*.

* * * * *